United States Patent
Hirano et al.

(10) Patent No.: US 6,852,856 B2
(45) Date of Patent: Feb. 8, 2005

(54) METHOD FOR PRESERVING QUATERNARY AMMONIUM SALT

(75) Inventors: Naoki Hirano, Tokuyama (JP); Masako Saijyo, Tokuyama (JP)

(73) Assignee: Tokuyama Corporation, Yamaguchi (JP)

(*) Notice: Subject to any disclaimer, the term of this patent is extended or adjusted under 35 U.S.C. 154(b) by 0 days.

(21) Appl. No.: 09/959,698

(22) PCT Filed: Mar. 9, 2001

(86) PCT No.: PCT/JP01/01877

§ 371 (c)(1),
(2), (4) Date: Nov. 5, 2001

(87) PCT Pub. No.: WO01/66528

PCT Pub. Date: Sep. 13, 2001

(65) Prior Publication Data

US 2003/0153785 A1 Aug. 14, 2003

(30) Foreign Application Priority Data

| Mar. 9, 2000 | (JP) | 2000-064959 |
| Apr. 24, 2000 | (JP) | 2000-122628 |
| Aug. 11, 2000 | (JP) | 2000-243558 |

(51) Int. Cl.$^7$ .............................. C07D 413/04
(52) U.S. Cl. ........................................ 544/113
(58) Field of Search ......................... 544/113

(56) References Cited

U.S. PATENT DOCUMENTS 3,826,788 A * 7/1974 Froehlich et al. .......... 260/91.3

OTHER PUBLICATIONS

Kunishima et al., Tetrahedron, 55(46), pp. 13159–13170, 1999.*

* cited by examiner

Primary Examiner—Richard L. Raymond
(74) Attorney, Agent, or Firm—Sherman & Shalloway

(57) ABSTRACT

A method of improving the stability of a quaternary ammonium salt and a method of efficiently preparing the quaternary ammonium salt having improved stability.

3 Claims, No Drawings

METHOD FOR PRESERVING QUATERNARY AMMONIUM SALT

This application is a 371 of PCT/JP01/01877, filed Mar. 1, 2002.

BACKGROUND ART

The present invention relates to a method of stably preserving a quaternary ammonium salt that is favorably used as a condensing agent for the preparation of amide compounds and ester compounds, to a method of preparing a stabilized quaternary ammonium salt, to a condensing agent using the stabilized quaternary ammonium salt as an effective component, and to a method of preparing amide compounds or ester compounds using the above condensing agent.

Amide compounds and ester compounds are very important compounds for forming basic skeletons of a variety of organic compounds such as medicines, agricultural chemicals, dyes and high-molecular compounds. Therefore, study has long been conducted concerning the method of preparing amide compounds and ester compounds. As methods of preparing amide compounds, for example, there have generally been known a method of preparing amide compounds by an exchange reaction of an ester compound with an amine compound, and a method of directly preparing amide compounds from a carboxylic acid compound and an amine compound. As the methods of preparing ester compounds, further, there have generally been known a method of directly preparing ester compounds from a carboxylic acid and an alcohol compound in the presence of an acid, and a method of preparing ester compounds by forming a carboxylic acid chloride by the reaction of a carboxylic acid compound with an acid-halogenating agent such as thionyl chloride, followed by being acted with an alcohol.

However, the method of preparing amide compounds is conducted under a heated condition, and cannot be conducted for preparing the compounds which are not thermally stable or for preparing compounds having both an amino group and an alkoxycarbonyl group in the same molecule. Further, the method of preparing ester compounds is conducted under an acidic condition, and cannot be conducted for preparing compounds which are not stable against acids.

In order to solve the above problems, there have been proposed various methods using a condensing agent such as a carbodiimide in order to prepare amide compounds under mild conditions. In particular, a 4-(4,6-dimethoxy-1,3,5-triazin-2-yl)-4-methylmorpholinium chloride proposed as a condensing agent for the synthesis of amide compounds by Z. J. Kaminski et al. {Journal of Organic Chemistry, Vol. 63, pp. 4248–4255, 1998} is drawing attention since it does not cause eruption that is caused by the carbodiimide-type condensing agent.

As for the preparation of ester compounds, further, a method of preparing ester compounds under mild conditions has been proposed by Mukaiyama et al by using a condensing agent comprising a pyridinium oxide compound {Bulletin of Chemical Society of Japan, Vol. 50, pp. 1863–1866, 1977}.

According to the method proposed by Kaminski et al. disclosed in the above literature, however, a carboxylic acid compound and a condensing agent are reacted together each in an amount of an equal mol to once form a reactive derivative which is an intermediate product and, then, the reactive derivative is reacted with an amine compound to obtain an amide compound. Therefore, the yield varies as widely as from 17 to 73%, which is far from satisfactory.

In preparing the above pyridinium oxide compound that is used for the preparation of ester compounds, further, it is necessary to use a methyl iodide which has been pointed out to be carcinogenic. Therefore, careful attention must be paid concerning the working environment.

In order to solve such problems, the present inventors have forwarded the study and have discovered that when a condensing agent comprising a quaternary ammonium salt represented by the following general formula (I),

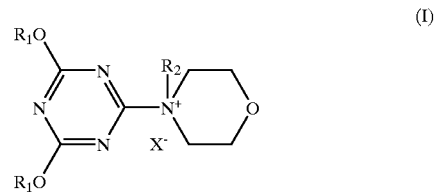

wherein $R^1$ is an alkyl group having 1 to 4 carbon atoms or an aryl group having 6 to 8 carbon atoms, $R^2$ is an alkyl group having 1 to 4 carbon atoms, and X is a halogen atom, a carboxylic acid compound and an amine compound are mixed and reacted together but without conducting the above-mentioned two-step reaction, then, the yield is improved, the reaction time is shortened and, besides, the condensing agent forms an amide compound in a high yield in a protonic organic solvent unlike the carbodiimide-type condensing agent which is the most widely used condensing agent (Japanese Patent Application No. 60765/1999, PCT/JP00/00834).

As for preparing the ester compounds, the inventors have discovered that the ester compounds can be prepared under mild conditions when a carboxylic acid compound is reacted with an alcohol compound by using the same condensing agent as the one used for the above-mentioned method of preparing the amide compounds proposed by the present inventors (Japanese Patent Application No. 137693/1999, PCT/JP00/00834).

While forwarding the study concerning the condensation reaction by using a quaternary ammonium salt represented by the above-mentioned general formula (I), however, the present inventors have noticed that the quaternary ammonium salt involves a problem concerning the stability. Namely, it became obvious that the quaternary ammonium salt undergoes the decomposition reaction during the preparation, preservation or use thereof. This means that the quaternary ammonium salt not only loses its purity and yield of condensation but also requires attention concerning its preservation and handling.

Usually, further, the quaternary ammonium salt represented by the above-mentioned general formula (I) can be prepared by reacting a triazine compound and a morpholine compound of corresponding structures together in an organic solvent. With this method, however, the reaction is not completed even after the passage of a long period of time and, as a result, the quaternary ammonium salt prepared by this method contains unreacted triazine compound in an amount of from about 1 to about 5%.

DISCLOSURE OF THE INVENTION

It is therefore an object of the present invention to provide a method of improving stability of a quaternary ammonium salt represented by the above-mentioned general formula (I), and a method of efficiently preparing the quaternary ammonium salt having improved stability.

In order to solve the above assignment, the present inventors have conducted a keen study, and have discovered the fact that when a triazine compound and a morpholine compound are reacted together in an organic solvent containing a particular amount of water, there is obtained a hydrate containing a quaternary ammonium salt of a high purity within short periods of time and, besides, the hydrous quaternary ammonium salt that is obtained is not easily decomposed exhibiting improved stability. Based on this discovery, the inventors have further forwarded the study, and have discovered that:

(i) the quaternary ammonium salt that contains water at a relatively small proportion can be stably preserved for extended periods of time even at room temperature, and can in its state be used as a condensing agent even after preserved;

(ii) the quaternary ammonium salt containing large amounts of water like, for example, an aqueous solution, is not almost decomposed in the aqueous solution even after freeze-preserved for extended periods of time and is thawed, and can be used as a condensing agent in the form of an aqueous solution;

(iii) the quaternary ammonium hydrate prepared by the above-mentioned method does not almost contain the unreacted triazine compound, and the quaternary ammonium salt obtained by removing water from the above hydrate can be stably preserved at a low temperature of not higher than 10° C. and, besides, even the quaternary ammonium salt obtained by the reaction in the absence of water can be preserved highly stably when it is highly purified to contain the triazine compound in a very small amount; and (iv) the quaternary ammonium salt containing the triazine compound in a very small amount is obtained even by using an alcohol in the above-mentioned method instead of using water;

and have thus accomplished the invention.

That is, a first invention is concerned with a method of preserving a quaternary ammonium salt represented by the following general formula (I),

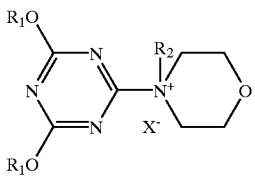

(I)

wherein $R^1$ is an alkyl group having 1 to 4 carbon atoms or an aryl group having 6 to 8 carbon atoms, $R^2$ is an alkyl group having 1 to 4 carbon atoms, and X is a halogen atom, (a) in the form of a hydrous quaternary ammonium salt containing 60 to 99% by weight of said quaternary ammonium salt and 40 to 1% by weight of water;

(b) by dissolving 100 parts by weight of said quaternary ammonium salt in 200 to 4000 parts by weight of water, and by freezing the thus obtained aqueous solution; or (c) by decreasing the content of a triazine compound represented by the following general formula (II),

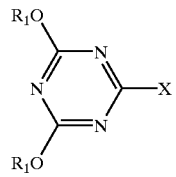

(II)

wherein $R^1$ is an alkyl group having 1 to 4 carbon atoms or an aryl group having 6 to 8 carbon atoms, and X is a halogen atom, contained as an impurity in the quaternary ammonium salt down to smaller than 1% by weight, and preserving said quaternary ammonium salt at a temperature of not higher than 25° C.

According to the above preservation method of the present invention, the quaternary ammonium salt represented by the above-mentioned general formula (I) can be stably preserved for extended periods of time.

A second invention is concerned with a hydrous quaternary ammonium salt containing 60 to 99% by weight of a quaternary ammonium salt represented by the above-mentioned general formula (I) and 40 to 1% by weight of water. A third invention is concerned with a quaternary ammonium salt represented by the above-mentioned general formula (I) synthesized by using, for example, a triazine compound represented by the above-mentioned formula (II) as a starting material, and containing the triazine compound in an amount of smaller than 1% by weight. These quaternary ammonium salts are highly stable and are not easily decomposed. Among the quaternary ammonium salts of the above third invention, the one having a water content of smaller than 1% by weight can be stably preserved for extended periods of time even in the absence of water. When used in the non-aqueous systems, therefore, the quaternary ammonium salt offers such an advantage that it does not require the drying operation prior to its use.

A fourth invention is concerned with a method of preparing a quaternary ammonium salt of the above second or third invention comprising reacting a triazine compound represented by the above-mentioned general formula (II) with a morpholine compound represented by the following general formula (III),

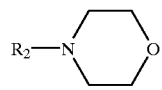

(III)

wherein $R^2$ is an alkyl group having 1 to 4 carbon atoms, in an organic solvent in the presence of water of an amount of from 0.1 to 10 mols per mol of the triazine compound. According to this preparation method, the object product is efficiently prepared within short periods of time. According to this preparation method, it is considered that the reaction is promoted due to water present in the reaction system and, at the same time, decomposition of the quaternary ammonium salt that is formed is suppressed contributing to shortening the reaction time and enhancing the purity.

A fifth invention is concerned with a method of preparing a quaternary ammonium salt of the above third invention containing water in an amount of smaller than 1% by weight comprising reacting a triazine compound represented by the above-mentioned general formula (II) with a morpholine compound represented by the above-mentioned general formula (III) in an organic solvent other than the alcohol in the presence of water or an alcohol of an amount of from 0.1 to 10 mols per mol of the triazine compound, and removing the organic solvent and water or the alcohol.

A sixth invention is concerned with a condensing agent comprising a hydrous quaternary ammonium salt of the above third invention. A seventh invention is concerned with a condensing agent containing 100 parts by weight of a quaternary ammonium salt represented by the above-mentioned general formula (I) and 200 to 4000 parts by weight of water. An eighth invention is concerned with a condensing agent comprising a quaternary ammonium salt represented by the above-mentioned general formula (I)

containing the triazine compound represented by the above-mentioned general formula (II) in an amount of smaller than 1% by weight.

A ninth invention and a tenth invention are, respectively, concerned with a method of preparing an amide compound by reacting a carboxylic acid compound with an amine compound by using one of those condensing agent, and a method of preparing an ester compound by reacting a carboxylic acid compound and an alcohol compound by using one of those condensing agent.

According to the method of preparing carboxylic acid compound derivatives (amide compounds or ester compounds) by using the condensing agent of the present invention, the quaternary ammonium salt does not decompose during the reaction and the yield of reaction is improved in addition to obtaining the effects that are accomplished when there is used a condensing agent comprising a quaternary ammonium salt represented by the above-mentioned general formula (I) taught in the above-mentioned Japanese Patent Application No. 60765/1999 or 137693/1999 (PCT/JP00/00834).

BEST MODE FOR CARRYING OUT THE INVENTION

The preservation method of the present invention preserves a quaternary ammonium salt represented by the above-mentioned general formula (I). Here, $R^1$ in the above-mentioned general formula (I) is an alkyl group having 1 to 4 carbon atoms or an aryl group having 6 to 8 carbon atoms, and $R^2$ is an alkyl group having 1 to 4 carbon atoms. As the alkyl group having 1 to 4 carbon atoms, there can be exemplified a methyl group, an ethyl group, an n-propyl group, an isopropyl group, an n-butyl group and an isobutyl group. As the aryl group having 6 to 8 carbon atoms, there can be exemplified a phenyl group, a tolyl group and a xylyl group. Among them, a methyl group or an ethyl group is preferably used as the alkyl group, and a phenyl group is preferably used as an aryl group from the standpoint of easy synthesis.

In the above-mentioned general formula (I), further, X is a halogen atom which may be fluorine, chlorine, bromine or iodine. Among them, chlorine is preferably used from the standpoint of easy synthesis.

Concrete examples of the quaternary ammonium salt represented by the above-mentioned general formula (I) of the present invention include 4-(4,6-dimethoxy-1,3,5-triazin-2-yl)-4-methylmorpholinium chloride, 4-(4,6-diethoxy-1,3,5-triazin-2-yl)-4-methylmorpholinium chloride, 4-(4,6-dipropoxy-1,3,5-triazin-2-yl)-4-methylmorpholinium chloride, 4-(4,6-diisopropoxy-1,3,5-triazin-2-yl)-4-methylmorpholinium chloride, 4-(4,6-dibutoxy-1,3,5-triazin-2-yl)-4-methylmorpholinium chloride, 4-(4,6-diphenoxy-1,3,5-triazin-2-yl)-4-methylmorpholinium chloride, 4-(4,6-dimethoxy-1,3,5-triazin-2-yl)-4-ethylmorpholinium chloride, 4-(4,6-diethoxy-1,3,5-triazin-2-yl)-4-ethylmorpholinium chloride, 4-(4,6-dipropoxy-1,3,5-triazin-2-yl)-4-ethylmorpholinium chloride, 4-(4,6-diisopropoxy-1,3,5-triazin-2-yl)-4-ethylmorpholinium chloride, 4-(4,6-dibutoxy-1,3,5-triazin-2-yl)-4-ethylmorpholinium chloride, 4-(4,6-diphenoxy-1,3,5-triazin-2-yl)-4-ethylmorpholinium chloride, 4-(4,6-dimethoxy-1,3,5-triazin-2-yl)-4-isobutylmorpholinium chloride, 4-(4,6-diethoxy-1,3,5-triazin-2-yl)-4-isobutylmorpholinium chloride, 4-(4,6-dipropoxy-1,3,5-triazin-2-yl)-4-isobutylmorpholinium chloride, 4-(4,6-diisopropoxy-1,3,5-triazin-2-yl)-4-isobutylmorpholinium chloride, 4-(4,6-dibutoxy-1,3,5-triazin-2-yl)-4-isobutylmorpholinium chloride, and 4-(4,6-diphenoxy-1,3,5-triazin-2-yl)-4-isobutylmorpholinium chloride.

Among them, it is particularly preferred to use 4-(4,6-dimethoxy-1,3,5-triazin-2-yl)-4-methylmorpholinium chloride, 4-(4,6-diethoxy-1,3,5-triazin-2-yl)-4-methylmorpholinium chloride, 4-(4,6-dipropoxy-1,3,5-triazin-2-yl)-4-methylmorpholinium chloride, 4-(4,6-diphenoxy-1,3,5-triazin-2-yl)-4-methylmorpholinium chloride, 4-(4,6-dimethoxy-1,3,5-triazin-2-yl)-4-ethylmorpholinium chloride, 4-(4,6-diethoxy-1,3,5-triazin-2-yl)-4-ethylmorpholinium chloride, 4-(4,6-dipropoxy-1,3,5-triazin-2-yl)-4-ethylmorpholinium chloride, and 4-(4,6-diphenoxy-1,3,5-triazin-2-yl)-4-ethylmorpholinium chloride, since they are easy to synthesize, and high condensation yields can be expected when they are used as condensing agents.

In the preservation method of the present invention, the quaternary ammonium salt represented by the above-mentioned general formula (I) must be preserved satisfying any one of the following conditions (a) to (c); i.e.,
(a) in the form of a hydrous quaternary ammonium salt containing 60 to 99% by weight of said quaternary ammonium salt and 40 to 1% by weight of water;
(b) by dissolving 100 parts by weight of said quaternary ammonium salt in 200 to 4000 parts by weight of water, and by freezing the thus obtained aqueous solution; or
(c) by decreasing the content of a triazine compound represented by the above-mentioned general formula (II) contained as an impurity in the quaternary ammonium salt down to smaller than 1% by weight and preserving the quaternary ammonium salt at a temperature of not higher than 25° C.

When preserved for extended periods of time without satisfying any one of these conditions, the decomposition cannot be avoided during the preservation.

These conditions will now be described in detail.

The condition (a) will be described, first. Under the above condition (a), the quaternary ammonium salt represented by the above-mentioned general formula (I) contains 40 to 1% by weight of water on the basis of the total amount of the quaternary ammonium salt and water. When this condition is satisfied, the quaternary ammonium salt can be stably maintained for extended periods of time even at room temperature.

When the content of water is smaller than 1% by weight, the effect is not obtained to a satisfactory degree to improve the stability by suppressing the decomposition of the quaternary ammonium though it may vary depending upon the purity. When the content of water exceeds 40% by weight, on the other hand, the hydrous quaternary ammonium salt assumes a half-solid state which is not only difficult to handle but causes the quaternary ammonium salt to undergo the hydrolysis when it is preserved at room temperature. From the standpoint of handling and stability of the quaternary ammonium salt, therefore, it is desired that the hydrous quaternary ammonium salt contains water in an amount of from 3 to 35% by weight. The content of water can be measured by using a heat balance, a Carl-Fischer water meter or by an ordinary method of measuring the water content.

In the above-mentioned hydrous quaternary ammonium salt, there is no particular limitation on the form in which water exists; i.e., water may be contained in the form of water of crystallization or free water.

There is no particular limitation on the method of preparing the hydrous quaternary ammonium salt. Preferably, however, the hydrous quaternary ammonium salt is prepared by the following method (also referred to as preparation method 1).

That is, the hydrous quaternary ammonium salt is preferably obtained by reacting the triazine compound represented by the above-mentioned general formula (II) with the morpholine compound represented by the above-mentioned general formula (III) in an organic solvent in the presence of water in an amount of from 0.1 to 10 mols per mol of the triazine compound. Here, $R^1$ and X in the above-mentioned general formula (II) are the same as $R^1$ and X in the above-mentioned general formula (I), and $R^2$ in the above-mentioned general formula (III) is the same as $R^2$ in the above-mentioned general formula (I).

Concrete examples of the triazine compound (triazine derivative) represented by the above-mentioned general formula (II) that can be preferably used in the preparation method 1 include 2-chloro-4,6-dimethoxy-1,3,5-triazine, 2-chloro-4,6-diethoxy-1,3,5-triazine, 2-chloro-4,6-dipropoxy-1,3,5-triazine, 2-chloro-4,6-diisopropoxy-1,3,5-triazine, 2-chloro-4,6-di-n-butoxy-1,3,5-triazine, 2-chloro-4,6-diisobutoxy-1,3,5-triazine and 2-chloro-4,6-diphenoxy-1,3,5-triazine. Among them, there can be particularly preferably used 2-chloro-4,6-dimethoxy-1,3,5-triazine, 2-chloro-4,6-diethoxy-1,3,5-triazine, 2-chloro-4,6-dipropoxy-1,3,5-triazine and 2-chloro-4,6-diphenoxy-1,3,5-triazine which are easy to synthesize.

Some of these triazine compounds are available as industrial starting materials. Generally, however, the triazine compounds are obtained by reacting a cyanuric chloride with a corresponding alcohol in the presence of a sodium hydrogen carbonate.

As the morpholine compound represented by the above-mentioned general formula (III) preferably used in the preparation method 1, there can be exemplified 4-methylmorpholine, 4-ethylmorpholine and 4-isobutylmorpholine. These morpholine compounds are all easily available as reagents or as industrial starting materials.

In the preparation method 1, though there is no particular limitation on the amount of using the morpholine compound represented by the above general formula (III), the morpholine compound usually reacts at a rate of one mol per mol of the triazine compound represented by the above-mentioned general formula (II). In such an equimolar reaction, it is a generally accepted practice to use either one of them in a slightly excess amount so that the conversion of the other starting compound becomes 100%. In the preparation method of the present invention, too, the morpholine compound represented by the above-mentioned general formula (III) is preferably used in an amount of from 0.7 to 1.3 mols and, particularly, from 0.8 to 1.2 mols per mol of the triazine compound represented by the above-mentioned general formula (II).

As the organic solvent, any organic solvent can be used without limitation provided it does not impair the reaction. Concrete examples of the organic solvent that can be used for the reaction include ethers such as tetrahydrofuran, 1,4-dioxane, diethyl ether, and diisopropyl ether; halogenated aliphatic hydrocarbons such as methylene chloride, chloroform and carbon tetrachloride; esters such as ethyl acetate and propyl acetate; ketones such as acetone, methyl ethyl ketone and methyl isobutyl ketone; nitrites such as acetonitrile and propionitrile; aromatic hydrocarbons such as benzene, toluene and xylene; halogenated aromatic hydrocarbons such as chlorobenzene and dichlorobenzene; amides such as N,N-dimethylformamide and N,N-dimethylacetamide; aliphatic hydrocarbons such as hexane and heptane; carbonates such as dimethyl carbonate and the like; alcohols such as t-butyl alcohol and t-amyl alcohol; and dimethyl sulfoxides. Among them, there can be preferably employed those organic solvents with which high isolation yields can be expected; i.e., ethers such as tetrahydrofuran, 1,4-dioxane, diethyl ether and diisopropyl ether; halogenated aliphatic hydrocarbons such as methylene chloride and chloroform; esters such as ethyl acetate and propyl acetate; ketones such as acetone, methyl ethyl ketone and methyl isobutyl ketone; nitriles such as acetonitrile and propionitrile; aromatic hydrocarbons such as benzene, toluene and xylene; and carbonates such as dimethyl carbonate and the like.

There is no particular limitation on the amount of using the organic solvent in the preparation method 1. When the amount is too large, however, the yield decreases per a batch, which is not economical. When the amount is too small, on other hand, the stirring is impaired. Generally, therefore, it is desired that the concentration of the quaternary ammonium salt represented by the above-mentioned general formula (I) that is formed becomes from 0.1 to 60% by weight and, preferably, from 1 to 50% by weight.

In the preparation method 1, however, it is important that the water is made present in an amount of from 0.1 to 10 mols per mol of the triazine compound in reacting the triazine compound with the morpholine compound in the organic solvent in order to easily obtain, within short periods of time, the hydrous quaternary ammonium salt containing a quaternary ammonium of a high purity and a predetermined amount of water.

When the amount of water that is made present during the reaction lies outside the above-mentioned range and is too small, the effect is not exhibited to a sufficient degree to suppress the decomposition of the quaternary ammonium salt that takes place during the reaction. When the amount of water is too large, on the other hand, the yield decreases. From the standpoint of obtaining the effect (for shortening the reaction time and for increasing the purity), it is particularly desired that the amount of water to be made present is from 0.2 to 8 mols per mol of the triazine compound.

The reaction of the triazine compound with the morpholine compound in the preparation method 1 is conducted by bringing the two in contact with each other in an organic solvent containing a predetermined amount of water. It is desired to effect the stirring to evenly carry out the reaction within short periods of time. The reaction can usually be conducted in an open atmosphere. When the compounds that are used and the product have hygroscopic properties, however, the reaction is desirably conducted in the dry air that has passed through a drying pipe such as a calcium chloride pipe or in an inert gaseous atmosphere such as of nitrogen, helium or argon. The reaction can further be carried out in any one of the reduced pressure condition, normal pressure condition or elevated pressure condition.

There is no particular limitation on the reaction temperature. When the temperature is too low, however, the rate of reaction becomes low. When the temperature is too high, on the other hand, a side reaction is promoted. Usually, therefore, the reaction temperature is selected over a range of from −20 to 70° C. and, preferably, from −10 to 60° C. Though there is no particular limitation, the reaction time of from 0.1 to 10 hours is usually sufficient.

The thus formed quaternary ammonium salt represented by the above general formula (I) usually precipitates as crystals. Therefore, the solid component is separated by an ordinary solid-liquid separation method such as centrifugal separation, centrifugal filtration, pressurized filtration or reduced-pressure filtration, and is, then, dried by an ordinary drying method such as air-blow drying or reduced-pressure drying, to thereby obtain the quaternary ammonium salt. In this case, the desired amount of water is adjusted by adjusting the drying conditions. The content of water can further be adjusted by mixing water to the hydrous quaternary ammonium salt that is obtained.

When no crystal precipitates, the organic solvent that is used is removed as much as possible and, then, a solvent such as tetrahydrofuran is added thereto to obtain a slurry thereof to obtain the quaternary ammonium salt relying upon the above-mentioned method.

Next, the condition (b) will be described. Under the condition (b), 100 parts by weight of the quaternary ammonium salt represented by the above-mentioned formula (I) is dissolved in 200 to 4000 parts by weight of water, and the resulting aqueous solution is freeze-preserved.

When the amount of water is not larger than 200 parts by weight per 100 parts by weight of the quaternary ammonium salt, the quaternary ammonium salt does not completely dissolve in water but becomes like a paste which is not easy to handle and requires an increased amount of energy for cooling for suppressing the decomposition to a sufficient degree. When the amount of water exceeds 4000 parts by weight, on the other hand, the stability is not improved so much. Besides, an increase in the volume requires a cumbersome handling for preservation inclusive of a problem of preservation space. Besides, the quaternary ammonium salt which is an effective component is so diluted that it cannot be used even as a condensing agent. From the standpoint of easy handling and stability at the time of preservation and easiness of use as the condensing agent, it is desired that the amount of water is from 250 to 2000 parts by weight per 100 parts by weight of the quaternary ammonium salt.

The quaternary ammonium salt can be obtained in the form of a hydrate according to the preparation method 1. In this case, the amount of water contained in the hydrate is included in the above-mentioned amount of water. The above-mentioned aqueous solution can be easily prepared by mixing the quaternary ammonium salt and a predetermined amount of water (amount determined by taking the amount of water into consideration when the quaternary ammonium salt is a hydrate) together to dissolve the quaternary ammonium salt therein. In this case, the quaternary ammonium salt needs not necessarily be all dissolved but may be left undissolved in small amounts without at all hindering the preservation thereof or the use thereof as a condensing agent. Besides, an organic solvent and any other third component may be contained within a range in which they do not adversely affect the properties or the freezing point of when the aqueous solution is used as the condensing agent.

The above-mentioned aqueous solution is prepared by any customarily used mixing method without limitation. Preferably, however, it is desired to stir the mixture so as to become homogeneous by using a stirrer. In this case, the two may be simultaneously added into the mixing container or may be successively added into the mixing container so as to be mixed together. When the temperature is too high at the time of mixing, however, the quaternary ammonium salt undergoes the decomposition. It is therefore desired to mix them together at not higher than 30° C. and, particularly, at not higher than 10° C.

The quaternary ammonium salt in the form of an aqueous solution undergoes the decomposition when it is preserved for extended periods of time at temperatures higher than room temperature. When not used for extended periods of time, therefore, the quaternary ammonium salt must be preserved in a form of being frozen. The temperature for freeze preservation may be the one at which the aqueous solution freezes, usually, at not higher than 0° C. and, preferably, at not higher than −10° C. When the quaternary ammonium salt needs be preserved for only about several days, however, it may be preserved at a low temperature of about 5° C.

The quaternary ammonium salt in the form of the aqueous solution can be used as a condensing agent by being added to the reaction system in its own state without removing water therefrom. The condensing agent in the form of the aqueous solution is easy to prepare and handle, and can be easily measured for use. Therefore, the aqueous solution that is freeze-preserved can be used as a condensing agent exhibiting properties same as those of before being preserved through a simple operation of thawing. It is allowable to add the aqueous solution in its frozen state into the reaction system so that it is thawed in the reaction system. It is further possible to easily recover the quaternary ammonium salt by thawing the aqueous solution after freeze-preserved and, then, removing the water therefrom. In conducting this recovery operation, it is desired that no third component is added in the step of preparing the aqueous solution in order to maintain purity of the quaternary ammonium salt that is recovered.

Next, the condition (c) will be described. The condition (c) is to preserve the quaternary ammonium salt by decreasing the content of the triazine compound (usually, the triazine compound used as a starting material for synthesizing the quaternary ammonium salt) represented by the above-mentioned general formula (II) contained as an impurity in the quaternary ammonium salt represented by the above-mentioned formula (I) down to smaller than 1% by weight and at a temperature of not higher than 25° C. The above condition was determined based on a discovery that is described below. That is, as described above, the quaternary ammonium salt represented by the above-mentioned general formula (I) is, usually, prepared by reacting a triazine compound and a morpholine compound of corresponding structures together in an organic solvent. Except the case of the reaction under particular conditions as in the above preparation method 1, however, the above-mentioned reaction is not usually finished even after it is conducted for extended periods of time and, as a result, the quaternary ammonium salt that is prepared, usually, contains the unreacted triazine compound in an amount of from about 1 to about 5%. On the other hand, the triazine compound is not almost contained in the hydrous quaternary ammonium salt obtained through the reaction of the above preparation method 1 under the conditions in which the mol number of the morpholine compound is slightly in excess of the mol number of the triazine compound. Besides, even the hydrous quaternary ammonium salt from which the water is removed exhibits improved stability as compared with the one that contains the triazine compound.

The content (% by weight) of the triazine compound under the condition (c) stands for % by weight with respect to the weight of the quaternary ammonium salt represented by the above-mentioned general formula (I) from which the amount of water, such as the water of crystallization and adhered water, is removed but which contains impurities (the above-mentioned triazine compound and other impurities). From the standpoint of maintaining a high preservation stability, it is desired that the content of the triazine compound is not larger than 0.5% by weight.

The quaternary ammonium salt containing the triazine compound in an amount of smaller than 1% by weight exhibits a high preservation stability and can be preserved for about one month at 25° C. When preserved at a temperature of 10 to −30° C., it can be stably preserved for extended periods of time (several months or longer). The temperature range of 10 to −30° C. can be realized in an ordinary refrigerator or in a freezer. This means that the quaternary ammonium salt of the present invention can be stably preserved for several months in a general refrigerator. Even the quaternary ammonium salt containing water in an amount of smaller than 1% by weight and the triazine compound in an amount of not smaller than 1% by weight can be suppressed from being decomposed to some extent when it is preserved at a low temperature, but cannot be stably preserved for several months in an ordinary refrigerator.

Under the condition (c), there is no particular limitation on the method of decreasing the content of the triazine compound in the quaternary ammonium salt to be smaller than 1% by weight. For example, the conventional quaternary ammonium salt containing 1 to 5% by weight of the triazine compound can be refined by repetitively conducting the recrystallization while confirming the purity thereof by the liquid chromatography or the like. From the standpoint of preparation efficiency, however, it is desired to employ the above-mentioned preparation method 1 or a method of using an alcohol (hereinafter also referred to as preparation method 2) instead of water used in the preparation method 1. The reaction in this case is such that the molar ratio of the morpholine compound is slightly in excess of the molar ratio of the triazine compound.

In particular, when the quaternary ammonium salt is to be used in a substantially anhydrous state, a hydrate thereof is once obtained through the preparation method 1 and from which the water is removed. Or, the reaction is conducted according to the preparation method 2 followed by the removal of the alcohol or the solvent that was used as required. In either case, the quaternary ammonium salt usually precipitates as crystals. Therefore, the quaternary ammonium salt is obtained by separating the solid component by an ordinary solid-liquid separation method such as centrifugal separation, centrifugal filtering, pressurized filtering or reduced-pressure filtering (i.e., organic solvent and water or alcohol are roughly removed), and drying the solid component by an ordinary drying method such as air-blow drying or reduced-pressure drying to further remove the organic solvent and water or alcohol. When the reaction is conducted in the organic solvent in the presence of the alcohol only without using water, the solvent and the alcohol can be easily removed. For example, there can be easily obtained the quaternary ammonium salt containing the triazine compound in an amount of smaller than 1% by weight, containing water in an amount of smaller than 1% by weight {here, the content (% by weight) of water stands for % by weight of water with respect the total weight of the quaternary ammonium salt containing water and impurities (triazine compound and other impurities)}. When the crystals are not precipitated, the organic solvent that is used is removed as much as possible, a solvent such as hetrahydrofuran is added to prepare a slurry, and the quaternary ammonium salt is obtained through the above-mentioned method.

After preserved under any one of the above-mentioned conditions (a) to (c) contemplated by the present invention, the quaternary ammonium salt can in its form be used as a condensing agent by being simply thawed without the need of drying or effecting any particular activation processing.

That is, the condensing agent of the present invention can be favorably used for the preparation of an amide compound by the reaction of a carboxylic acid compound with an amine compound or for the preparation of an ester compound by the reaction of a carboxylic acid compound with an alcohol compound, like forming the conventional quaternary ammonium salt represented by the above-mentioned general formula (I). In this case, not only the decomposition of the quaternary ammonium salt is suppressed during the condensation reaction but also the yield is improved by about several % as compared to when the conventional quaternary ammonium salt containing not smaller than 1% by weight of the triazine compound as impurity but without containing water is used.

Described below are the methods of preparing the above compounds by using the condensing agent of the present invention.

(1) A method of preparing an amide compound by reacting a carboxylic acid compound with an amine compound by using a condensing agent of the present invention (also referred to as amide preparation method of the invention).

The amide preparation method of the present invention can be conducted in the same manner as a conventional method of using a condensing agent with the exception of using the condensing agent of the present invention as a condensing agent. For example, the quaternary ammonium salt in the condensing agent of the invention is reacted, first, with the carboxylic acid compound to form a reactive derivative which is an intermediate product which is then reacted with an amine compound. Or, without forming the reactive derivative, the condensing agent, the carboxylic acid compound and the amine compound may be mixed and reacted together. From the standpoint of the reaction yield and the reaction time, however, it is desired to employ the latter method which mixes and reacts the above three kinds of reaction reagents together.

In the present invention, there is no particular limitation on the amount of using the condensing agent, and its amount may be suitably determined depending upon the kind of the quaternary ammonium salt contained in the condensing agent, the amount thereof and the reaction system. The condensing agent of the present invention can be used for the amide preparation method of the present invention. From the standpoint of easy synthesis and a high yield of condensation when used as a condensing agent, however, it is desired that the condensing agent is a hydrous quaternary ammonium salt containing 60 to 99% by weight of the quaternary ammonium salt and 40 to 1% by weight of water and, particularly, containing 65 to 97% by weight of the quaternary ammonium salt and 35 to 3% by weight of water; an aqueous solution containing 100 parts by weight of the quaternary ammonium salt and 250 to 2000 parts by weight of water; or the quaternary ammonium salt containing the triazine compound in an amount of not larger than 0.5% by weight. As for the amount of use, in general, the condensation reaction is not finished when the amount of use of the condensing agent is too small. Or, the condensing agent reacts with the amine compound and the yield decreases when amount of use of the condensing agent is too large. It is, therefore, desired that the quaternary ammonium salt is used in an amount of from 0.9 to 1.3 mols and, particularly, from 0.95 to 1.2 mols per mol of the carboxylic acid compound.

Next, described below is the carboxylic acid compound used for the amide preparation method of the present invention.

As the carboxylic acid compound used in the present invention, there can be used any compound without limitation provided it has a carboxyl group.

Concrete examples of the compound include aliphatic carboxylic acid compounds such as acetic acid, propionic acid, 2,2-dimethylpropionic acid, butanoic acid, pentanoic acid, hexanoic acid, heptanoic acid, octanoic acid, nonanoic acid, decanoic acid, undecanoic acid, acrylic acid and methacrylic acid; aromatic carboxylic acid compounds such as benzoic acid, o-nitrobenzoic acid, m-nitrobenzoic acid, p-nitrobenzoic acid, o-chlorobenzoic acid, m-chlorobenzoic acid, p-chlorobenzoic acid, o-methoxybenzoic acid, m-methoxybenzoic acid, p-methoxybenzoic acid, 3-phenylpropionic acid, 3-phenyl-2-propenoic acid, 2-(4-methoxyphenyl)acetic acid, and 3-(4-hydroxyphenyl) propionic acid; 2-aminothiazoleacetic acid derivatives; and amino acid derivatives of which the amino group is protected.

In order to obtain a cephem-type compound as an amide compound according to the present invention, it is desired to use a 2-aminothiazolylacetic acid derivative represented by the following general formula (IV),

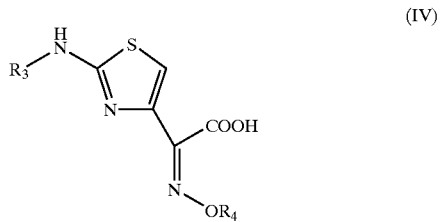

(IV)

wherein $R^3$ is a hydrogen atom, an acyl group, an alkoxycarbonyl group, an aralkyloxycarbonyl group or an aralkyl group, and $R^4$ is a hydrogen atom, an alkyl group, an aralkyl group, an acyl group or an alkoxycarbonylalkyl group, as a carboxylic acid compound.

Here, the cephem-type compound, generally, stands for a compound having a cephalosporanic acid in the molecules thereof. When the carboxylic acid compound comprising the above-mentioned 2-aminothiazolylacetic acid derivative is reacted with an amine compound comprising a 7-aminocephalosporanic acid derivative that will be described later, there can be prepared, as amide compounds, cephem-type compounds having structures corresponding to the starting materials that are used.

As the acyl group, alkoxycarbonyl group, aralkyloxycarbonyl group or aralkyl group represented by $R^3$ in the above-mentioned general formula (IV), there can be used any group without limitation provided it can be easily eliminated. Among these groups, concrete examples which are preferred include those acyl groups having 1 to 5 carbon atoms, such as formyl group, acetyl group, butylyl group, isobutylyl group, valeryl group and pivaloyl group; those alkoxycarbonyl groups having 2 to 7 carbon atoms, such as methoxycarbonyl group, ethoxycarbonyl group, propoxycarbonyl group, isopropoxycarbonyl group, tert-butoxycarbonyl group and tert-amyloxycarbonyl group; and those aralkyloxycarbonyl groups having 8 to 10 carbon atoms, such as benzyloxycarbonyl group and phenetyloxycarbonyl group. As the aralkyl group, there can be preferably used those having 7 to 20 carbon atoms, such as benzyl group, diphenylmethyl group and triphenylmethyl group.

Among them, there is particularly preferably used the acyl group such as formyl group or acetyl group, the alkoxycarbonyl group such as methoxycarbonyl group or tert-butoxycarbonyl group, the aralkyloxycarbonyl group such as benzyloxycarbonyl group, or the aralkyl group such as benzyl group or triphenylmethyl group from the standpoint of easy elimination reaction and a high yield of condensation.

As the alkyl group, aralkyl group, acyl group or alkoxycarbonylalkyl group represented by $R^4$, there can be used, without any limitation, a group that exhibits a pharmacological effect as a cephem compound or a hydrocarbon group that can be easily eliminated. Concrete examples include those alkyl groups having 1 to 4 carbon atoms, such as methyl group, ethyl group, propyl group, isopropyl group, butyl group, isobutyl group and tert-butyl group; those aralkyl groups having 7 to 20 carbon atoms, such as benzyl group, diphenylmethyl group and triphenylmethyl group; those acyl groups having 1 to 5 carbon atoms, such as formyl group, acetyl group, butyryl group, isobutylyl group, valeryl group and pivaloyl group; and those alkoxycarbonylalkyl groups having 3 to 8 carbon atoms, such as methoxycarbonylmethyl group, 1-methoxycarbonyl-1-methylethyl group, tert-butoxycarbonylmethyl group, and 1-tert-butoxycarbonyl-1-methyl ethyl group. Among them, there can be preferably employed those alkyl groups having 1 to 3 carbon atoms, such as methyl group, ethyl group and propyl group having a small steric hindrance.

Among the 2-aminothiazolylacetic acid derivatives represented by the above-mentioned general formula (IV), there can be preferably used those in which $R^3$ is a hydrogen atom, a benzyloxycarbonyl group, a tert-butoxycarbonyl group, a methoxycarbonyl group, a formyl group, a trityl group, an acetyl group, or a chloroacetyl group, and $R^4$ is a hydrogen atom, a methyl group, an ethyl group, a methoxycarbonylmethyl group, a 1-methoxycarbonyl-1-methyl ethyl group or a benzyl group from a standpoint of expecting a high pharmacological effect when the derivative is converted into a cephem-type compound that is being prepared. Concrete examples of the 2-aminothiazoleacetic acid derivatives represented by the above-mentioned general formula (IV) that can be preferably used include 2-(2-aminothiazol-4-yl)-2-methoxyiminoacetic acid, 2-(2-benzyloxycarbonyl-aminothiazol-4-yl)-2-methoxyiminoacetic acid, 2-(2-tert-butoxycarbonylaminothiazol-4-yl)-2-methoxyiminoacetic acid, 2-(2-methoxycarbonylaminothiazol-4-yl)-2-methoxyiminoacetic acid, 2-(2-formylaminothiazol-4-yl)-2-methoxyiminoacetic acid, 2-(2-tritylaminothiazol-4-yl)-2-methoxyiminoacetic acid, 2-(2-acetylaminothiazol-4-yl)-2-methoxyiminoacetic acid, 2-(2-chloroacetylaminothiazol-4-yl)-2-methoxyiminoacetic acid, 2-(2-aminothiazol-4-yl)-2-hydroxyiminoacetic acid, 2-(2-benzyloxycarbonyl-aminothiazol-4-yl)-2-hydroxyiminoacetic acid, 2-(2-tert-butoxycarbonylaminothiazol-4-yl)-2-hydroxyiminoacetic acid, 2-(2-methoxycarbonylaminothiazol-4-yl)-2-hydroxyiminoacetic acid, 2-(2-formylaminothiazol-4-yl)-2-hydroxyiminoacetic acid, 2-(2-tritylaminothiazol-4-yl)-2-hydroxyiminoacetic acid, 2-(2-acetylaminothiazol-4-yl)-2-hydroxyiminoacetic acid, 2-(2-aminothiazol-4-yl)-2-methoxycarbonylmethoxyiminoacetic acid, 2-(2-benzyloxycarbonylaminothiazol-4-yl)-2-methoxycarbonylmethoxyiminoacetic acid, 2-(2-tert-butoxycarbonylaminothiazol-4-yl)-2-methoxycarbonylmethoxyiminoacetic acid, 2-(2-methoxycarbonyl-aminothiazol-4-yl)-2-methoxycarbonylmethoxyiminoacetic acid, 2-(2-formylaminothiazol-4-yl)-2-methoxycarbonylmethoxyiminoacetic acid, 2-(2-tritylaminothiazol-4-yl)-2-methoxycarbonylmethoxyiminoacetic acid, 2-(2-acetylaminothiazol-4-yl)-2-methoxycarbonylmethoxyiminoacetic acid, 2-(2-chloroacetylaminothiazol-4-yl)-2-methoxycarbonylmethoxyiminoacetic acid, 2-(2-aminothiazol-4-yl)-2-(1-methoxycarbonyl-1-ethylethoxy) iminoacetic acid, 2-(2-benzyloxycarbonylaminothiazol-4-yl)-2-(1-methoxycarbonyl-1-methylethoxy)iminoacetic acid, 2-(2-tert-butoxycarbonylaminothiazol-4-yl)-2-(1- methoxycarbonyl-1-methylethoxy)iminoacetic acid, 2-(2-methoxycarbonylaminothiazol-4-yl)-2-(1-methoxycarbonyl-1-methylethoxy)iminoacetic acid, 2-(2-formylaminothiazol-4-yl)-2-(1-methoxycarbonyl-1-methyethoxy)iminoacetic acid, 2-(2-tritylaminothiazol-4-yl)-2-(1-methoxycarbonyl-1-methylethoxy)iminoacetic acid, 2-(2-acetylaminothiazol-4-yl)-2-(1-methoxycarbonyl-1-methylethoxy)iminoacetic acid, 2-(2-aminothiazol-4-yl)-2-benzyloxyiminoacetic acid, 2-(2-benzyloxycarbonylaminothiazol-4-yl)-2-benzyloxyiminoacetic acid, 2-(2-tert-butoxycarbonylaminothiazol-4-yl)-2-benzyloxyiminoacetic acid, 2-(2-methoxycarbonylaminothiazol-4-yl)-2-benzyloxyiminoacetic acid, 2-(2-formylaminothiazol-4-yl)-2-benzyloxyiminoacetic acid, 2-(2-tritylaminothiazol-4-yl)-2-benzyloxyiminoacetic acid, 2-(2-acetylaminothiazol-4-yl)-2-benzyloxyiminoacetic acid, 2-(2-aminothiazol-4-yl)-2-ethoxyiminoacetic acid, 2-(2-benzyloxycarbonylaminothiazol-4-yl)-2-ethoxyiminoacetic acid, 2-(2-tert-butoxycarbonylaminothiazol-4-yl)-2-ethoxyiminoacetic acid, 2-(2-methoxycarbonylaminothiazol-4-yl)-2-ethoxyiminoacetic acid, 2-(2-formylaminothiazol-4-yl)-2-ethoxyiminoacetic acid, 2-(2-tritylaminothiazol-4-yl)-2-ethoxyiminoacetic acid, 2-(2-acetylaminothiazol-4-yl)-2-ethoxyiminoacetic acid, and 2-(2-chloroacetylaminothiazol-4-yl)-2-ethoxyiminoacetic acid.

Among them, it is particularly desired, from the standpoint of expecting high yields of condensation, to use 2-(2-aminothiazol-4-yl)-2-methoxyiminoacetic acid, 2-(2-benzyloxycarbonylaminothiazol-4-yl)-2-methoxyiminoacetic acid, 2-(2-tert-butoxycarbonylaminothiazol-4-yl)-2-methoxyiminoacetic acid, 2-(2-methoxycarbonylaminothiazol-4-yl)-2-methoxyiminoacetic acid, 2-(2-formylaminothiazol-4-yl)-2-methoxyiminoacetic acid, 2-(2-tritylaminothiazol-4-yl)-2-methoxyiminoacetic acid, 2-(2-acetylaminothiazol-4-yl)-2-methoxyiminoacetic acid, 2-(2-chloroacetylaminothiazol-4-yl)-2-methoxyiminoacetic acid, 2-(2-aminothiazol-4-yl)-2-methoxycarbonylmethoxyiminoacetic acid, 2-(2-benzyloxycarbonylaminothiazol-4-yl)-2-methoxycarbonylmethoxyiminoacetic acid, 2-(2-tert-butoxycarbonylaminothiazol-4-yl)-2-methoxycarbonylmethoxyiminoacetic acid, 2-(2-methoxycarbonylaminothiazol-4-yl)-2-methoxycarbonylmethoxyiminoacetic acid, 2-(2-formylaminothiazol-4-yl)-2-methoxycarbonylmethoxyiminoacetic acid, 2-(2-acetylaminothiazol-4-yl)-2-methoxycarbonylmethoxyiminoacetic acid, 2-(2-aminothiazol-4-yl)-2-(1-methoxycarbonyl-1-methylethoxy)iminoacetic acid, 2-(2-benzyloxycarbonylaminothiazol-4-yl)-2-(1-methoxycarbonyl-1-methylethoxy)iminoacetic acid, 2-(2-tert-butoxycarbonylaminothiazol-4-yl)-2-(1-methoxycarbonyl-1-methylethoxy)iminoacetic acid, 2-(2-methoxycarbonylaminothiazol-4-yl)-2-(1-methoxycarbonyl-1-methylethoxy)iminoacetic acid, 2-(2-formylaminothiazol-4-yl)-2-(1-methoxycarbonyl-1-methylethoxy)iminoacetic acid, 2-(2-acetylaminothiazol-4-yl)-2-(1-methoxycarbonyl-1-methylethoxy)iminoacetic acid, 2-(2-aminothiazol-4-yl)-2-benzyloxyiminoacetic acid, 2-(2-benzyloxycarbonylaminothiazol-4-yl)-2-benzyloxyiminoacetic acid, 2-(2-tert-butoxycarbonylaminothiazol-4-yl)-2-benzyloxyiminoacetic acid, 2-(2-methoxycarbonylaminothiazol-4-yl)-2-benzyloxyiminoacetic acid, 2-(2-formylaminothiazol-4-yl)-2-benzyloxyiminoacetic acid, 2-(2-acetylaminothiazol-4-yl)-2-benzyloxyiminoacetic acid, 2-(2-aminothiazol-4-yl)-2-ethoxyiminoacetic acid, 2-(2-benzyloxycarbonylaminothiazol-4-yl)-2-ethoxyiminoacetic acid, 2-(2-tert-butoxycarbonylaminothiazol-4-yl)-2-ethoxyiminoacetic acid, 2-(2-methoxycarbonylaminothiazol-4-yl)-2-ethoxyiminoacetic acid, 2-(2-formylaminothiazol-4-yl)-2-ethoxyiminoacetic acid, and 2-(2-acetylaminothiazol-4-yl)-2-ethoxyiminoacetic acid.

Among the 2-aminothiazolylacetic acid derivatives represented by the above-mentioned general formula (IV), there theoretically exist two kinds of isomers concerning the oxyimino group, i.e., syn(z)-isomers and anti(E)-isomers. Either one of them can be used for the present invention. When used for the 7-aminocephalosporanic acid derivatives, however, the syn-isomers are desired from the standpoint of expecting a higher pharmacological activity.

These 2-aminothiazolylacetic acid derivatives can be easily synthesized from the starting materials that are industrially available. For example, use is made, as a starting material, of a 2-aminothiazolylacetic acid ester compound which is available as a reagent or as an industrial starting material, such as ethyl 2-(2-aminothiazol-4-yl)-2-methoxyiminoacetate, ethyl 2-(2-aminothiazol-4-yl)-2-hydroxyiminoacetate, ethyl 2-(2-aminothiazol-4-yl)-2-(1-methoxycarbonyl-1-methylethoxyiminoacetate or 2-(2-aminothiazol-4-yl)-2-methoxycarbonylmethoxyiminoacetate which, as required, is acted by an amino group-protecting agent such as acetyl chloride, chloroacetyl chloride, trityl chloride, benzyloxycarbonyl chloride, methoxycarbonyl chloride, di-tert-butyl dicarbonate, methyl formate or ethyl formate to protect the amino group. As required, further, the hydroxyimino group is protected by using a hydroxyl group-protecting agent such as dimethylsulfuric acid, diethylsulfuric acid, benzylchloride or benzyl bromide, followed by hydrolysis to prepare the 2-aminothiazolylacetic acid derivatives.

When it is attempted to obtain a peptide compound which is very important as a pharmaceutical intermediate product by the method of preparing amide of the present invention, it is desired to use a derivative of an amino acid compound of which the amino group is protected as a carboxylic acid compound.

The peptide compound, generally, stands for a compound having two or more amino acids in the molecules thereof. When there are used a derivative of an amino acid compound of which the amino group is protected as a carboxylic acid compound and a derivative of an amino acid compound of which the carboxyl group, that will be described later, is protected as an amine compound, there can be prepared, as amide compounds, peptide compounds having structures corresponding to the starting materials that are used.

As the derivative of the amino acid compound of which the amino group is protected, there can be used any compound without limitation provided it has an amino group and a carboxyl group in the molecules and provided the amino group thereof is protected by a protection group. Generally, however, there is used an amino acid compound of which the amino group is protected and which is easily available as a reagent or as an industrial starting material.

Here, examples of the protection group include formyl group, acetyl group, benzoyl group, benzyloxycarbonyl group, tert-butoxycarbonyl group, allyloxycarbonyl group, methoxycarbonyl group, trityl group and fluorenylmethoxycarbonyl group.

Concrete examples of the derivative of the amino acid compound of which the amino group is protected by the protection group and which can be favorably used for the preparation of the peptide compound include α-aminobutanoic acid, α-methylalanine, alanine, N-methylalanine, β-alanine, γ-aminobutanoic acid, 5-aminopentanoic acid, 6-aminohexanoic acid, 7-aminohexanoic acid, 8-aminooctanoic acid, 11-aminoundecanoic acid, 12-aminoundecanoic acid, arginine, asparagine, aspartic acid, β-cyclohexylalanine, cyclohexylglycine, S-acetamidecystein, S-tert-butylcystein, S-ethylthiocystein, S-p-methoxybenzylcystein, S-tritylcystein, S-p-methylbenzylhomocystein, glutamine, N-γ-ethylglutamine, N-γ-tritylglutamine, glutamic acid, isoglutamic acid, glycine, N-methylglycine, histidine, π-benzyloxymethylhistidine, 1-methylhistidine, 3-methylhistidine, isoleucine, leucine, N-methylleucine, lizine, N-ε-acetylleucine, N-ε-formylleucine, N-ε-benzyloxycarbonylleucine, methionine, norleucine, norvaline, ornithine, 4-benzoylphenylalanine, phenylalanine, 4-chlorophenylalanine, 4-fluorophenylalanine, 4-benzyloxycarbonylaminophenylalanine, homophenylalanine, phenylglycine, 4-hydroxyphenylglycine, proline, homoproline, 4-hydroxyproline, O-benzylhydroxyproline, N-methylglycine, homoserine, O-benzylhomoserine, O-benzylserine, serine, tert-butylserine, O-methylserine, threonine, O-benzylthreonine, tryptophane, tyrosine, O-tert-butyltyrosine, O-benzyltyrosine and valine.

Many of the above-mentioned amino acids have asymmetric carbon atoms. In the present invention, there can be used L-isomers, D-isomers and a mixture thereof without any limitation.

These compounds are usually available as reagents and industrial starting materials. When not available, however, the compounds can be prepared by adding a tertiary amine such as methylmorpholine or a triethylamine to the above amino acid in an organic solvent, and protecting the amino group by using an amino group-protecting agent such as methyl formate, ethyl formate, acetyl chloride, anhydrous acetic acid, benzoyl chloride, benzyloxycarbonyl chloride, di-tert-butyl dicarbonate, tert-butoxycarbonyl fluoride, diallyl dicarbonate, methoxycarbonyl chloride, trityl chloride, or fluorenylmethoxycarbonyl chloride, followed by neutralization and precipitation.

Next, described below are the amine compounds used for the method of preparing amide of the present invention.

As the amine compound used in the present invention, there can be used a compound having a primary amino group or a secondary amino group without limitation.

Concrete examples of the amine compound used in the present invention include aliphatic amine compounds such as methylamine, ethylamine, 1-propylamine, isopropylamine, 1-butylamine, isobutylamine, sec-butylamine, 1,2-dimethylpropylamine, tert-butylamine, 1-pentylamine, 1-hexylamine, 2-ethylhexylamine, 1-heptylamine, 1-octylamine, 1-nonylamine, 1-decanylamine, 1-undecanylamine, dimethylamine, diethylamine, diisopropylamine, allylamine, diallylamine, pyrrolidine, 3-hydroxypyrrolidine, piperidine, 2-pipecoline, 3-pipecoline, 4-pipecoline, 2,4-lupetidine, 2,6-lupetidine, 3,5-lupetidine, M-methylhomopiperazine, N-acylhomopiperazine, N-methylpiperazine, N-ethoxycarbonylpiperazine, p-chlorophenylpiperazine, 1-(2-pyrimidyl)piperazine, 1-amino-4-cyclohexylpiperazine, 1-cyclohexylpiperazine, 3-hydroxymethylpiperizine, N-aminopiperizine, N-aminopipecoline, 2-hydroxyethylpiperizine, hydroxyethylamine, 3-hydroxypropylamine, 2-hydroxyropylamine, 1-hydroxy-2-propylamine, 3-methoxypropylamine, 3-ethoxypropylamine, 3-butoxypropylamine, 3-(2-ethylhexyloxy)propylamine, 3-decyloxypropylamine, 3-lauloxypropylamine, 3-myristiloxypropylamine, dimethylaminoethylamine, diethylaminoethylamine, dimethylaminopropylamine, dibutylaminopropylamine, dimethylaminoethoxypropylamine and methoxyamine; aromatic amine compounds such as aniline, benzylamine, dibenzylamine, α-phenetylamine, β-phenetylamine, 2-aminothiazole, 2-aminopyridine, 3-aminopyridine, 4-aminopyridine, indole, N-(2-pyridyl)piperazine, furfurylamine, 2-aminopyrazine, 2-amino-5-methylpyridine, 2-amino-6-methylpyridine and 2-amino-4,6-dimethylpyridine; 7-aminocephalosporanic acid derivatives; and amino acid derivatives of which the carboxyl group is protected.

Among these compounds as described above, it is desired to use a 7-aminocephalosporanic acid derivative for obtaining a cephem compound. AS the 7-aminocephalosporanic acid derivative that can be preferably used, there can be exemplified a compound represented by the following general formula (V)

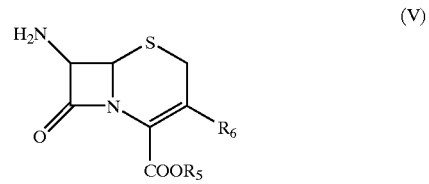

(V)

wherein $R^5$ is an alkyl group, an aralkyl group, an aryl group, an alkoxycarbonylalkyl group, an alkoxycarbonyloxyalkyl group, an alkylcarbonyloxyalkyl group or a trialkylsilyl group, and $R^6$ is a hydrogen atom, a methoxymethyl group, a chlorine atom, an iodomethyl group, a vinyl group, an acetyloxymethyl group, a 2-furalcarbonylthiomethyl group, a (1,2,3-thiadiazol-5-yl)thiomethyl group, a (1-methyltetrazol-5-yl) thiomethyl group, a (5-methyltetrazol-3-yl)methyl group, a (Z)-2-(1,2,3-thiadiazol-4-yl)ethenyl group, a (Z)-2-(4-methylthiazol-5-yl)ethenyl group, or a (1H-1,2,3-triazol-5-yl)thiomethylthio group.

As the alkyl group, aralkyl group, aryl group, alkoxycarbonylalkyl group, alkoxycarbonyloxyalkyl group, alkylcarbonyloxyalkyl group or trialkylsilyl group represented by $R^5$ in the above general formula (V), there can be used the one that can be easily hydrolyzed without any limitation. Concrete examples that can be preferably used include those lower alkyl groups having 1 to 4 carbon atoms, such as methyl group, ethyl group, propyl group, isopropyl group, butyl group, isobutyl group and tert-butyl group; those aralkyl groups having 7 to 20 carbon atoms, such as benzyl group, diphenylmethyl group and triphenylmethyl group; those aryl groups having 6 to 8 carbon atoms, such as phenyl group and tolyl group; those alkoxycarbonylalkyl groups such as methoxycarbonylmethyl group, 1-methoxycarbonyl-1-methyl ethyl group and tert-butoxycarbonylmethyl group; those alkoxycarbonyloxyalkyl groups having 3 to 10 carbon atoms, such as 1-tert-butoxycarbonyloxyethyl group, 1-cyclohexyloxycarbonyloxyethyl group and 1-ethoxycarbonyloxyethyl group; those alkylcarbonyloxyalkyl group having 3 to 10 carbon atoms, such as methylcarbonyloxymethyl group, ethylcarbonyloxymethyl group and tert-butylcarbonyloxymethyl group; and those trialkylsilyl groups having 3 to 9 carbon atoms, such as trimethylsilyl group, triethylsilyl group and tert-butyldimethylsilyl group.

Among these groups, it is particularly desired, from the standpoint of easy chemical or physiological hydrolysis, to use those lower alkyl groups having 1 to 4 carbon atoms, such as methyl group, ethyl group, propyl group, isopropyl group, butyl group, isobutyl group and tert-butyl group;

those alkoxycarbonylalkyl groups such as ethoxycarbonylmethyl group, 1-methoxycarbonyl-1-methyl ethyl group and tert-butoxycarbonylmethyl group; those alkoxycarbonyloxyalkyl groups having 3 to 10 carbon atoms, such as 1-tert-butoxycarbonyloxyethyl group, 1-cyclohexylcarbonyloxyethyl group and 1-ethoxycarbonyloxyethyl group; and those trialkylsilyl groups having 3 to 9 groups, such as trimethylsilyl group, triethylsilyl group and t-butyldimethylsilyl group.

Concrete examples of the 7-aminocephalosporanoic acid derivative represented by the above-mentioned general formula (V) that can be preferably used include methyl 7-amino-3-cephem-4-carboxylate, methyl 7-amino-3-chloro-3-cephem-4-carboxylate, methyl 7-amino-3-iodomethyl-3-cephem-4-carboxylate, methyl 7-amino-3-vinyl-3-cephem-4-carboxylate, methyl 7-amino-3-acetyloxymethyl-3-cephem-4-carboxylate, methyl 7-amino-3-(2-furalcarbonylthiomethyl)-3-cephem-4-carboxylate, methyl 7-amino-3-[(1,2,3-thiadiazol-5-yl)thiomethyl]-3-cephem-4-carboxylate, methyl 7-amino-3-[(1-methyltetrazol-5-yl)thiomethyl]-3-cephem-4-carboxylate, methyl 7-amino-3-[(Z)-2-(1,2,3-thiadiazol-4-yl)ethenyl]-3-cephem-4-carboxylate, methyl 7-amino-3-[(5-methyltetrazol-3-yl)methyl]-3-cephem-4-carboxylate, methyl 7-amino-3-[(Z)-2-(4-methylthiazol-5-yl)ethenyl]-3-cephem-4-carboxylate, methyl 7-amino-3-[(1H-1,2,3-triazol-5-yl)thiomethylthio]-3-cephem-4-carboxylate, ethyl 7-amino-3-cephem-4-carboxylate, ethyl 7-amino-3-chloro-3-cephem-4-carboxylate, ethyl 7-amino-3-iodomethyl-3-cephem-4-carboxylate, ethyl 7-amino-3-vinyl-3-cephem-4-carboxylate, ethyl 7-amino-3-acetyloxymethyl-3-cephem-4-carboxylate, ethyl 7-amino-3-(2-furalcarbonylthiomethyl)-3-cephem-4-carboxylate, ethyl 7-amino-3-[(1,2,3-thiadiazol-5-yl)thiomethyl]-3-cephem-4-carboxylate, ethyl 7-amino-3-[(1-methyltetrazol-5-yl)thiomethyl]-3-cephem-4-carboxylate, ethyl 7-amino-3-[(Z)-2-(1,2,3-thiadiazol-4-yl)ethenyl]-3-cephem-4-carboxylate, ethyl 7-amino-3-[(5-methyltetrazol-3-yl)methyl]-3-cephem-4-carboxylate, ethyl 7-amino-3-[(Z)-2-(4-methylthiazol-5-yl)ethenyl]-3-cephem-4-carboxylate, ethyl 7-amino-3-[(1H-1,2,3-triazol-5-yl)thiomethylthio]-3-cephem-4-carboxylate, isopropyl 7-amino-3-cephem-4-carboxylate, isopropyl 7-amino-3-chloro-3-cephem-4-carboxylate, isopropyl 7-amino-3-iodomethyl-3-cephem-4-carboxylate, isopropyl 7-amino-3-binyl-3-cephem-4-carboxylate, isopropyl 7-amino-3-acetyloxymethyl-3-cephem-4-carboxylate, isopropyl 7-amino-3-(2-furalcarbonylthiomethyl)-3-cephem-4-carboxylate, isopropyl 7-amino-3-[(1,2,3-thiadiazol-5-yl)thiomethyl]-3-cephem-4-carboxylate, isopropyl 7-amino-3-[(1-methyltetrazol-5-yl)thiomethyl]-3-cephem-4-carboxylate, isopropyl 7-amino-3-[(Z)-2-(1,2,3-thiadiazol-4-yl)ethenyl]-3-cephem-4-carboxylate, isopropyl 7-amino-3-[(5-methyltetrazol-3-yl )methyl]-3-cephem-4-carboxylate, isopropyl 7-amino-3-[(Z)-2-(4-methylthiazol-5-yl)ethenyl]-3-cephem-4-carboxylate, isopropyl 7-amino-3-[(1H-1,2,3-triazol-5-yl)thiomethylthio]-3-cephem-4-carboxylate, tert-butyl 7-amino-3-cephem-4-carboxylate, tert-butyl 7-amino-3-chloro-3-cephem-4-carboxylate, tert-butyl 7-amino-3-iodomethyl-3-cephem-4-carboxylate, tert-butyl 7-amino-3-vinyl-3-cephem-4-carboxylate, tert-butyl 7-amino-3-acetyloxymethyl-3-cephem-4-carboxylate, tert-butyl 7-amino-3-(2-furalcarbonylthiomethyl)-3-cephem-4-carboxylate, tert-butyl 7-amino-3-[(1,2,3-thiadiazol-5-yl)thiomethyl]-3-cephem-4-carboxylate, tert-butyl 7-amino-3-[(1-methyltetrazol-5-yl)thiomethyl]-3-cephem-4-carboxylate, tert-butyl 7-amino-3-[(Z)-2-(1,2,3-thiadiazol-4-yl)ethenyl]-3-cephem-4-carboxylate, tert-butyl 7-amino-3-[(5-methyltetrazol-3-yl)methyl]-3-cephem-4-carboxylate, tert-butyl 7-amino-3-[(Z)-2-(4-methylthiazol-5-yl)ethenyl]-3-cephem-4-carboxylate, tert-butyl 7-amino-3-[(1H-1,2,3-triazol-5-yl)thiomethylthio]-3-cephem-4-carboxylate, methyl 7-amino-3-cephem-4-carboxylate, methoxycarbonylmethyl 7-amino-3-chloro-3-cephem-4-carboxylate, methoxycarbonylmethyl 7-amino-3-iodomethyl-3-cephem-4-carboxylate, methoxycarbonylmethyl 7-amino-3-binyl-3-cephem-4-carboxylate, methoxycarbonylmethyl 7-amino-3-acetyloxymethyl-3-cephem-4-carboxylate, methoxycarbonylmethyl 7-amino-3-(2-furalcarbonylthiomethyl)-3-cephem-4-carboxylate, methoxycarbonylmethyl 7-amino-3-[(1,2,3-thiadiazol-5-yl)thiomethyl]-3-cephem-4-carboxylate, methoxycarbonylmethyl 7-amino-3-[(1-methyltetrazol-5-yl)thiomethyl]-3-cephem-4-carboxylate, methoxycarbonylmethyl 7-amino-3-[(Z)-2-(1,2,3-thiadiazol-4-yl)ethenyl]-3-cephem-4-carboxylate, methoxycarbonylmethyl 7-amino-3-[(5-methyltetrazol-3-yl)methyl]-3-cephem-4-carboxylate, methoxycarbonylmethyl 7-amino-3-[(Z)-2-(4-methylthiazol-5-yl)ethenyl]-3-cephem-4-carboxylate, methoxycarbonylmethyl 7-amino-3-[(1H-1,2,3-triazol-5-yl)thiomethylthio]-3-cephem-4-carboxylate, diphenylmethyl 7-amino-3-cephem-4-carboxylate, diphenylmethyl 7-amino-3-chloro-3-cephem-4-carboxylate, diphenylmethyl 7-amino-3-iodomethyl-3-cephem-4-carboxylate, diphenylmethyl 7-amino-3-binyl-3-cephem-4-carboxylate, diphenylmethyl 7-amino-3-acetyloxymethyl-3-cephem-4-carboxylate, diphenylmethyl 7-amino-3-(2-furalcarbonylthiomethyl)-3-cephem-4-carboxylate, dipheylmethyl 7-amino-3-[(1,2,3-thiadiazol-5-yl)thiomethyl]-3-cephem-4-carboxylate, diphenylmethyl 7-amino-3-[(1-methyltetrazol-5-yl)thiomethyl]-3-cephem-4-carboxylate, diphenylmethyl 7-amino-3-[(Z)-2-(1,2,3-thiadiazol-4-yl)ethenyl]-3-cephem-4-carboxylate, diphenylmethyl 7-amino-3-[(5-methyltetrazol-3-yl)methyl]-3-cephem-4-carboxylate, diphenylmethyl 7-amino-3-[(Z)-2-(4-methylthiazol-5-yl)ethenyl]-3-cephem-4-carboxylate, diphenylmethyl 7-amino-3-[(-1H-1,2,3-triazol-5-yl)thiomethylthio]-3-cephem-4-carboxylate, trimethylsilyl 7-amino-3-cephem-4-carboxylate, trimethylsilyl 7-amino-3-chloro-3-cephem-4-carboxylate, trimethylsilyl 7-amino-3-iodomethyl-3-cephem-4-carboxylate, trimethylsilyl 7-amino-3-vinyl-3-cephem-4-carboxylate, trimethylsilyl 7-amino-3-acetyloxymethyl-3-cephem-4-carboxylate, trimethylsilyl 7-amino-3-(2-furalcarbonylthiomethyl)-3-cephem-4-carboxylate, trimethylsilyl 7-amino-3-[(1,2,3-thiadiazol-5-yl)thiomethyl]-3-cephem-4-carboxylate, trimethylsilyl 7-amino-3-[(1-methyltetrazol-5-yl)thiomethyl]-3-cephem-4-carboxylate, trimethylsilyl 7-amino-3-[(Z)-2-(1,2,3-thiadiazol-4-yl)ethenyl]-3-cephem-4-carboxylate, trimethylsilyl 7-amino-3-[(5-methyltetrazol-3-yl)methyl]-3-cephem-4-carboxylate, trimethylsilyl 7-amino-3-[(Z)-2-(4-methylthiazol-5-yl)ethenyl]-3-cephem-4-carboxylate, and -trimethylsilyl 7-amino-3-[(1H-1,2,3-triazol-5-yl)thiomethylthio]-3-cephem-4-carboxylate.

These compounds are prepared by using a 7-amino-3-acetyloxymethyl-3-cephem-4-carboxylic acid which is easily and industrially available as a starting material, converting the third position by a predetermined substituent and esterifying the carboxyl group.

In order to obtain the peptide compound, further, it is desired to use, as an amine compound, an amino acid compound derivative of which the carboxyl group is protected as described earlier. As the amino acid compound derivative of which the carboxyl group is protected, there can be used, without limitation, any compound having an amino group and a carboxyl group in the molecules, the carboxyl group being protected by a protection group. In general, however, there is used an amino acid compound which is easily available as a reagent or as an industrial starting material and of which the carboxylic acid is protected.

Here, the protection group for the carboxyl group is, for example, an alkyl group having 1 to 4 carbon atoms, such as methyl group, ethyl group, propyl group, isopropyl group or t-butyl group, an aralkyl group having 6 to 13 carbon atoms, such as benzyl group or diphenylmethyl group, or an amino group, an N-methylamino group or an N-benzylamino group.

Concrete examples of the amino acid compound derivative of which the carboxyl group is protected and which is desirably used for obtaining the peptide compound, include α-aminobutanoic acid, α-methylalanine, alanine, N-methylalanine, β-alanine, γ-aminobutanoic acid, 5-aminopentanoic acid, 6-aminohexanoic acid, 7-aminohexanoic acid, 8-aminooctanoic acid, 11-aminoundecanoic acid, 12-aminoundanoic acid, arginine, asparagine, aspartic acid, β-cyclohexylalanine, cyclohexylglycine, S-acetamidecystein, S-tert-butylcystein, S-ethylthiocystein, S-p-methoxybenzylcystein, S-tritylcystein, S-p-methylbenzylhomocystein, glutamine, N-γ-ethylglutamine, N-γ-ethylglutamine, N-γ-tritylglutamine, glutamic acid, isoglutamic acid, glycine, N-methylglycine, histidine, π-benzyloxymethylhistidine, 1-methylhistidine, 3-methylhistidine, isoleucine, leucine, N-methylleucine, lizine, N-ε-acetylleucine, N-ε-formylleucine, N-ε-benzyloxycarbonylleucine, methionine, norleucine, norvaline, ornithine, 4-benzoylphenylalanine, phenylalanine, 4-chlorophenylalanine, 4-fluorophenylalanine, 4-benzyloxycarbonylaminophenylalanine, homophenylalanine, phenylglycine, 4-hydroxyphenylglycine, proline, homoproline, 4-hydroxyproline, O-benzylhydroxyproline, N-methylglycine, homoserine, O-benzylhomoserine, O-benzylserine, serine, tert-butylserine, O-methylserine, threonine, O-benzylthreonine, triprophane, tyrosine, O-tert-butyltyrosine, O-benzyltyrosine and valine.

Many of these amino acids have asymmetric carbon atoms. In the present invention, the L-isomers, D-isomers and a mixture thereof can be used without any limitation.

These compounds are usually available as reagents and industrial starting materials. When not available, however, they can be prepared by transforming the above amino acid into an acid chloride with a thionyl chloride or the like, followed by the reaction with an alkyl alcohol compound having 1 to 4 carbon atoms, such as methanol, ethanol, propanol, isopropanol or tert-butanol, with an aralkyl alcohol compound having 7 to 13 carbon toms, such as benzyl alcohol or diphenylmethyl alcohol, or with ammonia or a primary or a secondary amine having 1 to 10 carbon atoms, such as methylamine, ethylamine or benzylamine.

There is no particular limitation on the amounts of using the carboxylic acid compound and the amine compound in the method of preparing amide of the present invention. However, the reaction of the carboxyl group with the amino group according to the preparation method (hereinafter also referred to as amide-forming reaction) is a stoichiometric reaction. In the reaction of the compounds each having a group in a number of one in the molecules thereof, however, it is usually desired to use the amine compound in an amount of from 0.8 to 1.2 mols and, preferably, from 0.9 to 1.1 mols per mol of the carboxylic acid compound.

It is desired that the amide-forming reaction is conducted in a solvent. Here, any solvent that is industrially used can be used without limitation. Concrete examples of the solvent include water; ethers such as tetrahydrofurane, 1,4-dioxane, diethyl ether and tert-butylmethyl ether; esters such as ethyl acetate, propyl acetate and butyl acetate; nitrites such as acetonitrile and propionitrile; halogenated aliphatic hydrocarbons such as methylene chloride, chloroform and carbon tetrachloride; alcohols such as methanol, ethanol, isopropanol and tert-butanol; ketones such as acetone, methyl ethyl ketone, and methyl isobutyl ketone; carbonates such as dimethyl carbonate; aromatic hydrocarbons such as benzene, toluene and xylene; halogenated aromatic hydrocarbons such as chlorobenzene; amides such as dimethylformamide and dimethylacetamide; and dimethylsulfoxide.

Among these solvents, it is desired to use, from the standpoint of expecting high yields of condensation, ethers such as tetrahydrofurane, 1,4-dioxane, diethyl ether and tert-butyl methyl ether; esters such as ethyl acetate, propyl acetate and butyl acetate; nitrites such as acetonitrile and propionitrile; halogenated aliphatic hydrocarbons such as methylene chloride and chloroform; alcohols such as methanol, ethanol, isopropanol and tert-butanol; ketones such as acetone, methyl ethyl ketone and methylisobutyl ketone; carbonates such as dimethyl carbonate, etc.; aromatic hydrocarbons such as benzene, toluene and xylene; and water. These solvents may be used alone or being mixed together.

There is no particular limitation on the concentrations of the carboxylic acid compound and the amine compound in the solvent. When the concentrations are too low, however, the yield of the amide compound is small per a time of reaction, which is not economical. When the concentrations are too high, on the other hand, the stirring is impaired. Usually, therefore, the concentrations should be so selected that the concentration of the formed amide compound in the solvent is from 0.1 to 80% by mass and, preferably, from 1 to 60% by mass.

Next, described below is the procedure of operation of the method of preparing amide according to the present invention.

In the method of preparing amide of the present invention as described above, the amide-forming reaction may be conducted in the same manner as the conventional method of using a condensing agent but using a hydrous quaternary ammonium salt of the present invention as a condensing agent, and there is no particular limitation on the procedure of operation. From the standpoint of increasing the reaction yield and shortening the reaction time, however, it is desired to effect the reaction by mixing three kinds of reaction agents (i.e., condensing agent, carboxylic acid compound and amine compound) together. Here, the above-mentioned three components may be reacted together by being mixed together, but need not exist necessarily in their forms in the reaction system. For example, the carboxylic acid compound and the amine compound may be neutralized and may exist in the form of salts.

In the above-mentioned method, there is no particular limitation on the method of mixing the above three kinds of reaction reagents. That is, the components may be simultaneously added to the reaction system and may be mixed. Or, the reaction reagents may be successively added to the reaction system and may be mixed. From the standpoint of operability and reaction yield, however, it is desired to add the reaction agents successively maintaining short time intervals into the reaction solvent that has been maintained at a predetermined temperature to mix them together. Here, no limitation is imposed on the order of adding the reaction reagents. Generally, however, it is considered that what is important is to form the salt in the solvent by the neutralization reaction of the carboxylic acid compound with the amine compound. Generally, therefore, the condensing agent is added after the carboxylic acid compound and the amine compound have been added.

Either the carboxylic acid compound or the amine compound may be added first. When the two are mixed together, however, there takes place the neutralization reaction, and the heat of neutralization is usually generated. Immediately after the two compounds are added, therefore, it is likely that the temperature is elevated in the reaction system. Therefore, if the condensing agent is readily added thereto, the amine compound may react with the condensing agent causing the yield to be dropped. It is, hence, desired to add the condensing agent after the carboxylic acid compound and the amine compound have been added and mixed and after the temperature of the reaction system has been lowered down to a predetermined temperature. Or, it is desired to lower the temperature of the solvent down to a sufficient degree in advance at the time of adding the carboxylic acid compound and the amine compound.

The optimum reaction temperature for the amide-forming reaction greatly differs depending upon the kinds of the carboxylic acid compound and the amine compound that are used, and cannot be exclusively specified. When the temperature is too low, however, the reaction rate becomes low and when the temperature is too high, a side reaction may occur causing the amine compound to react with the condensing agent. It is therefore desired that the reaction temperature lies in a range of from −30 to 60° C. and, particularly, from −20 to 50° C.

The reaction time may be suitably determined depending upon the kinds of the carboxylic acid compound and the amine compound that are used, but is, usually, from 0.1 to 8 hours and, preferably, from 1 to 6 hours. The amide-forming reaction can be carried out under any one of the conditions of normal pressure, elevated pressure or reduced pressure.

The thus obtained amide compound can be isolated and refined by an ordinary method without any limitation. Described below are concrete methods. That is, when an organic solvent that is not compatible with water is used as the reaction solvent, the reaction solution, after the reaction has been finished, is washed with an acidic aqueous solution, an alkaline aqueous solution or water and, then, the solvent is distilled away. The amide compound is, then, isolated and refined by recrystallization or silica gel chromatography. When an organic solvent that is compatible with water is used as the reaction solvent, the reaction solution, after the reaction has been finished, is exchanged by an organic solvent that is not compatible with water, and the above-mentioned method is conducted to isolate and refine the amide compound. When the water is used as the solvent, further, an organic solvent that is not compatible with water is added to extract the amide compound in the organic phase and, then, the above-mentioned method is conducted to isolate and refine the amide compound. Thus, the amide compound is industrially advantageously prepared.

(2) Preparation of an ester compound by the reaction of a carboxylic acid compound with an alcohol compound by using the condensing agent of the invention (hereinafter also referred to as an ester preparation method of the invention).

The ester preparation method of the present invention can be conducted in the same manner as a conventional method of using a condensing agent with the exception of using the condensing agent of the present invention as a condensing agent. It is, here, desired to mix the condensing agent of the present invention, a carboxylic acid compound and an alcohol compound and react them together in the presence of a tertiary amine (hereinafter also referred to as an esterification reaction). The rate of esterification reaction can be elevated by making the tertiary amine compound present.

In this case, there is no particular limitation on the amount of using the condensing agent of the present invention, and the amount of use may be suitably determined depending upon the reaction system. The condensing agents of the present invention can be used for the ester preparation method of the present invention. Among them, it is desired to use the condensing agent that is preferably used for the amide preparation method of the present invention, since it can be easily synthesized and offers an expectation of a high yield of condensation. The amount of use of the condensing agent is such that when its amount is too small, the condensation reaction is not finished and when its amount is too large, the reaction occurs with the alcohol compound causing the yield to decrease. It is therefore desired that the quaternary ammonium salt is used in an amount of from 0.9 to 3 mols and, particularly, from 0.95 to 2.5 mols per mol of the carboxylic acid compound.

Described below is the carboxylic acid compound that is used in the present invention.

As the carboxylic acid compound, there can be used an aliphatic carboxylic acid compound, an aromatic carboxylic acid compound and an amino acid compound derivative of which the amino group is protected, which are the same as those used for the amide preparation method of the present invention. Among them, it is desired to use the amino acid compound derivative of which the amino group is protected from such a standpoint that the esterification reaction that undergoes under mild conditions is very effective in esterifying a compound that is subject to undergo the decomposition reaction due to the heat. Concrete examples therefore are the same as those exemplified in the description of the amide preparation method of the present invention.

As the alcohol compound used in the ester preparation method of the present invention, further, there can be used the compounds having primary, secondary and tertiary hydroxyl groups without limitation. Concrete examples of the alcohol compound that can be preferably used include aliphatic alcohol compounds having 1 to 10 carbon atoms, such as methanol, ethanol, 1-propanol, 2-propanol, 1-butanol, 2-butanol, 2-methyl-2-propanol, 1-pentanol, 2-pentanol, 3-pentanol, 2-methyl-2-pentanol, 3-methyl-3-pentanol, cyclopropanol, cyclopentanol, cyclohexanol and cycloheptanol; and aromatic alcohol compounds having 6 to 12 carbon atoms, such as phenol, o-cresol, m-cresol, p-cresol, benzyl alcohol, 2-phenyl-1-ethanol, 1-phenyl-1-ethanol and 3-phenyl-1-propanol.

Among these alcohols, it is particularly desired to use methanol, ethanol, 1-propanol, 1-butanol, 1-pentanol, cyclopropanol, cyclopentanol, cyclohexanol, cycloheptanol, phenol, p-cresol, benzyl alcohol, 2-phenyl-1-ethanol and 3-phenyl-1-propanol, enabling the esterification reaction to easily proceed. These alcohol compounds are all available as industrial starting materials or reagents.

In the ester preparation method of the present invention, there is no particular limitation on the amounts of the carboxylic acid compound and the alcohol compound that are used. Considering the fact that the hydroxyl group of the alcohol compound stoichiometrically reacts with the carboxyl group of the carboxylic acid compound and that the alcohol compound itself serves as a solvent, however, there is no particular limitation on the upper limit of amounts when there is used a monohydric alcohol in an amount of, usually, not smaller than an equivalent to the carboxyl groups of the carboxylic acid compound. When the amount of the alcohol compound becomes too large relative to the carboxylic acid compound, however, the yield of the ester compound becomes small per a batch, which is not economical. It is therefore desired to use the alcohol compound in such an amount that the concentration of the carboxylic acid compound in the alcohol compound is not smaller than 0.1% by weight.

Any tertiary amine compound can be used, as required, for the ester preparation method of the present invention provided it has a tertiary amino group. Concrete examples of the tertiary amine compound that can be preferably used include aliphatic tertiary amines such as 4-methylmorpholine, 4-ethylmorpholine, N-methylpyrrolidine, N-ethylpyrrolidine, N-methylpiperidine, N-ethylpiperidine, N-methylindolin, N-methylisoindolin, triethylamine, tribuylamine, dimethylisopropylamine, dimethylcyclohexylamine, N,N,N',N'-tetramethylethylenediamine, N,N,N',N'-tetramethylpropanediamine and N,N,N',N'-tetramethylbutanediamine; and aromatic tertiary amines such as pyridine, N,N-dimethylaniline, N,N-diethylaniline, N,N-dimethylbenzylamine, N,N-diethylbenzylamine, N-methylindole, N-methylisoindole, N-methylpyrrole, indolizine and N-methylcarbazole. Among them, it is particularly desired to use 4-methylmorpholine, 4-ethylmorpholine, N-methylpyrrolidine, N-ethylpyrolidine, N-methylpiperidine, N-ethylpiperidine, triethylamine, tributylamine, dimehylisopropylamine, dimethylcyclohexylamine, pyridine, N,N-dimethylaniline, N,N-diethylaniline, N,N-dimethylbenzylamine and N,N-diethylbenzylamine.

These tertiary amine compounds are all available as industrial starting materials or reagents.

There is no particular limitation on the amount of the tertiary amine compound that is sued. From the standpoint of the rate of reaction and the operability of isolation from the ester compound after the reaction, however, it is desired to use the tertiary amine compound in an amount of from 0.01 to 3 mols and, particularly from 0.05 to 2 mols per mol of the carboxylic acid compound.

In the ester preparation method of the present invention, the esterification reaction is carried out, usually, by using the alcohol as a solvent provided the melting point of the alcohol compound that is used is not higher than 0° C. The esterification reaction, however, can be conducted even by using other organic solvents. As the organic solvent used for the esterification reaction, there can be used any solvent that is industrially used without limitation. As the solvent that can be used, there can be exemplified those which are the same as those used for the amide preparation method of the present invention. Further, the solvents that are preferably used for the amide preparation method of the invention can also be used here on account of the same reason as that of the case of the amide preparation method. In using the solvent, further, there is no particular limitation on the concentrations of the carboxylic acid compound and the alcohol compound in the solvent. From the standpoint of the reaction rate and the yield per a batch, however, it is desired that their concentrations are so selected that the concentration of the formed ester compound in the solvent is, usually, from 0.1 to 80% by weight and, preferably, from 1 to 60% by weight.

There is no particular limitation on the procedure of operation of when the condensing agent comprising the hydrous quaternary ammonium salt of the present invention, carboxylic acid compound and alcohol compound are mixed and reacted together in the presence of the tertiary amine compound. For example, the components may be simultaneously added to the reaction system and mixed, or the components may be successively added to the reaction system and mixed. From the standpoint of operability and the yield of reaction, however, it is desired to successively add the components into the reaction solvent maintained at a predetermined temperature in a short time interval, so as to be mixed together. In this case, there is no particular limitation on the order of adding the four components. Generally, however, it is considered that what is important is to form a salt in the solution by the neutralization reaction of the carboxylic acid compound with the tertiary amine compound. Generally, therefore, the alcohol compound and the condensing agent are added after the carboxylic acid compound and the tertiary amine compound have been added.

Either the carboxylic acid compound or the tertiary amine compound may be added first. When the two are mixed together, however, there takes place the neutralization reaction, and the heat of neutralization usually generates. Immediately after the two compounds are added, therefore, it is likely that the temperature is elevated in the reaction system. Therefore, if the alcohol compound and the condensing agent are readily added thereto, the alcohol compound may react with the condensing agent causing the yield to be dropped. It is, hence, desired to add the condensing agent after the carboxylic acid compound and the tertiary amine compound have been added and mixed and after the temperature of the reaction system has been lowered down to a predetermined temperature. Or, it is desired to lower the temperature of the solvent down to a sufficient degree in advance at the time of adding the carboxylic acid compound and the tertiary amine compound.

The optimum reaction temperature for the esterification reaction greatly differs depending upon the kinds of the carboxylic acid compound and the amine compound that are used, and cannot be exclusively specified. When the temperature is too low, however, the reaction rate becomes low and when the temperature is too high, a side reaction in which the alcohol compound reacts with the condensing agent may occur. It is therefore desired that the reaction temperature lies in a range of from −30 to 60° C. and, particularly, from −20 to 50° C.

The reaction time may be suitably determined depending upon the kind and amount of the alcohol compound, but is, usually, from 0.1 to 40 hours and, preferably, from 1 to 24 hours. The reaction can be carried out under any one of the conditions of normal pressure, elevated pressure or reduced pressure.

The thus obtained ester compound can be isolated and refined by an ordinary method without any limitation. Described below are concrete methods. That is, when an organic solvent that is not compatible with water is used as the reaction solvent, the reaction solution, after the reaction has been finished, is washed with an acidic aqueous solution, an alkaline aqueous solution or water and, then, the solvent is dried. The ester compound is, then, isolated and refined by recrystallization or silica gel chromatography. When an organic solvent that is compatible with water is used as the reaction solvent, the reaction solution, after the reaction has been finished, is exchanged with an organic solvent that is not compatible with water, and the above-mentioned method is conducted to isolate and refine the ester compound. When the water is used as the solvent, further, an organic solvent that is not compatible with water is added to extract the ester compound in the organic phase and, then, the above-mentioned method is conducted to isolate and refine the ester compound.

Thus, the ester compound is industrially advantageously prepared.

EXAMPLES

The present invention will now be described by way of Examples to which only, however, the invention is in no way limited.

Example 1

Into a 2000-ml four neck distillation flask were added 87.8 g (0.5 mols) of a 2-chloro-4,6-dimethoxy-1,3,5-triazine, 1000 ml of an ethyl acetate and 27 g (1.5 mols) of water, which were then stirred at 5 to 10° C. for 10 minutes. Next, 53.1 g (0.525 mols) of a 4-methylmorpholine was added thereto to conduct the reaction at 5 to 10° C. for 6 hours. The conversion of the triazine compound at this moment was nearly 100%. The precipitated crystals were filtrated by means of suction, washed with 400 ml of the ethyl acetate and was dried at room temperature under a reduced pressure for 4 hours to obtain 141.7 g of a white solid of a 4-(4,6-dimethoxy-1,3,5-triazin-2-yl)-4-methylmorpholinium chloride. The amount of water was 8.4% by weight and the yield was 93.8%.

Analysis by using a high-performance liquid chromatography indicated the purity of the product to be 99.5% in terms of area %. The product was, then, preserved at 20 to 25° C. for 3 weeks and was measured for its purity to be 98.0%.

Examples 2 to 4

The operation was carried out in the same manner as in Example 1 but effecting the drying for periods of time shown in Table 1. The results were as shown in Table 1.

TABLE 1

| Example | Drying time | Water content | Yield | Purity | Purity after 3 weeks |
| --- | --- | --- | --- | --- | --- |
| 2 | 14 hrs | 1.6% by mass | 94.1% | 99.5% | 96.5% |
| 3 | 10 hrs | 5.0% by mass | 93.8% | 99.4% | 97.5% |
| 4 | 3 hrs | 12.8% by mass | 93.3% | 99.5% | 99.1% |

Example 5

Into a 2000-ml four neck distillation flask were added 87.8 g (0.5 mols) of a 2-chloro-4,6-dimethoxy-1,3,5-triazine, 1000 ml of an ethyl acetate and 27 g (1.5 mols) of water, which were then stirred at 5 to 10° C. for 10 minutes. Next, 53.1 g (0.525 mols) of a 4-methylmorpholine was added thereto, and the mixture was stirred at 5 to 10° C. for 6 hours. Further, water was added thereto in an amount of 27 g (1.5 mols) and the mixture was stirred for 10 minutes. The conversion of the triazine compound at this moment was nearly 100%. The precipitated crystals were filtrated by means of suction, washed with 400 ml of the ethyl acetate and was dried at room temperature under a reduced pressure for 4 hours to obtain 159.4 g of a white solid of a 4-(4,6-dimethoxy-1,3,5-triazin-2-yl)-4-methylmorpholinium chloride. The amount of water was 19.1% by weight and the yield was 93.2%.

Analysis by using a high-performance liquid chromatography indicated the purity of the product to be 99.5% in terms of area %. The product was, then, preserved at 20 to 25° C. for 3 weeks and was measured for its purity to be 98.7%.

Example 6

Into a 2000-ml four neck distillation flask were added 87.8 g (0.5 mols) of a 2-chloro-4,6-dimethoxy-1,3,5-triazine, 1000 ml of an ethyl acetate and 27 g (1.5 mols) of water, which were then stirred at 5 to 10° C. for 10 minutes. Next, 53.1 g (0.525 mols) of a 4-methylmorpholine was added thereto, and the mixture was stirred at 5 to 10° C. for 6 hours. Further, water was added thereto in an amount of 54 g (3.0 mols) and the mixture was stirred for 10 minutes. The conversion of the triazine compound at this moment was nearly 100%. The precipitated crystals were filtrated by means of suction, washed with 400 ml of the ethyl acetate and was dried at room temperature under a reduced pressure for 7 hours to obtain 176.7 g of a white solid of a 4-(4,6-dimethoxy-1,3,5-triazin-2-yl)-4-methylmorpholinium chloride. The amount of water was 28.6% by weight and the yield was 91.2%.

Analysis by using a high-performance liquid chromatography indicated the purity of the product to be 99.2% in terms of area %. The product was, then, preserved at 20 to 25° C. for 3 weeks and was measured for its purity to be 98.5%.

Example 7

100 Grams of the 4-(4,6-dimethoxy-1,3,5-triazin-2-yl)-4-methylmorpholinium chloride having a water content of 8.4% by weight obtained in Example 1 and 14.5 g of water were mixed together to obtain the 4-(4,6-dimethoxy-1,3,5-triazin-2-yl)-4-methylmorpholinium chloride having a water content of 20.0% by weight.

Analysis by using a high-performance liquid chromatography indicated the purity of the product to be 99.3% in terms of area %. The product was, then, preserved at 20 to 25° C. for 3 weeks and was measured for its purity to be 98.6%.

Comparative Example 1

Into a 2000-ml four neck distillation flask were added 87.8 g (0.5 mols) of a 2-chloro-4,6-dimethoxy-1,3,5-triazine and 1000 ml of an ethyl acetate, which were then stirred at 5 to 10° C. for 10 minutes. Next, 53.1 g (0.525 mols) of a 4-methylmorpholine was added thereto, and the mixture was stirred at 5 to 10° C. for 24 hours. The precipitated crystals were filtrated by means of suction, washed with 400 ml of the ethyl acetate and was dried at room temperature under a reduced pressure for 4 hours to obtain 131.3 g of a white solid of a 4-(4,6-dimethoxy-1,3,5-triazin-2-yl)-4-methylmorpholinium chloride. The amount of water was 0.3% by weight and the yield was 94.6%. Six hours after the start of the reaction, the reaction solution was sampled in a small amount and was analyzed by using a high-performance liquid chromatography to find that the conversion of the triazine compound was about 93%.

Analysis by using a high-performance liquid chromatography indicated the purity of the product to be 95.4% in terms of area %. There remained 3.1% of the 2-chloro-4,6-dimethoxy-1,3,5-triazine that was the starting material. The product was, then, preserved at 20 to 25° C. for 3 weeks and was measured for its purity to be 89.8%.

Comparative Example 2

10 Grams of the 4-(4,6-dimethoxy-1,3,5-triazin-2-yl)-4-methylmorpholinium chloride having a water content of 8.4% by weight obtained in Example 1 and 8.32 g of water were mixed together to obtain the 4-(4,6-dimethoxy-1,3,5-triazin-2-yl)-4-methylmorpholinium chloride having a water content of 50.0% by weight.

Analysis by using a high-performance liquid chromatography indicated the purity of the product to be 99.0% in terms of area %. The product was, then, preserved at 20 to 25° for 3 weeks and was measured for its purity to be 31.3%.

From the comparison of Examples 1 to 7 with Comparative Example 1, it was learned that when the reaction was conducted by making present the water in an amount of from 0.1 to 10 mols per mol of the triazine compound (Examples 1 to 7), the reaction time was greatly shortened as compared to the case when the reaction was conducted without substantially using water (Comparative Example 1) and, besides, the obtained quaternary ammonium salt possessed an increased purity.

From the comparison of Example 1 to 7 with Comparative Examples 1 and 2, it was learned that when the amount of water in the quaternary ammonium salt was smaller than 1% by weight or in excess of 40% by weight, the stability was poor whereas when the amount of water was from 1 to 40% by weight, the stability was greatly improved.

Example 8

Into a 100-ml egg plant-type flask were added 3.00 g (0.02 mols) of a 3-phenylpropionic acid as a carboxylic acid compound, 2.42 g (0.02 mols) of a β-phenetylamine as an amine compound and 50 ml of a methylene chloride as a solvent, which were then stirred at room temperature for 10 minutes followed by the addition of 6.35 g (0.02 mols) of the same 4-(4,6-dimethoxy-1,3,5-triazin-2-yl)-4-methylmorpholinium chloride having a water content of 12.8% by weight as the one prepared in Example 4 as a condensing agent to effect the reaction at room temperature for 3 hours.

After the reaction, 100 ml of water was added thereto to separate the solution. Thereafter, the extraction operation was conducted twice with 30 ml of a methylene chloride. The separated methylene chloride solution was collected, and the organic layer was washed with 30 ml of a saturated sodium carbonate aqueous solution, 30 ml of a 1N hydrochloric acid and 30 ml of water. The obtained organic phase was dried on magnesium sulfate, the methylene chloride was distilled away, and the residue was isolated and refined by using a silica gel column chromatography to obtain 4.86 g of an N-(β-phenetyl)-3-phenylpropionic acid amide (yield, 96%).

Examples 9 to 35

Amide compounds were obtained by conducting the same operation as that of Example 8 but using the carboxylic acid compounds, amine compounds and solvents shown in Table 2. The results were as shown in Table 2.

TABLE 2

| Ex. | Carboxylic acid compound | Amine compound | Product | Solvent | Reaction time (hrs) | Yield (%) |
|---|---|---|---|---|---|---|
| 9 | 3-phenylpropionic acid | β-phenetylamine | N-(β-phenetyl)-3-phenylpropion amide | methanol | 3 | 92 |
| 10 | 3-phenylpropionic acid | β-phenetylamine | N-(β-phenetyl)-3-phenylpropion amide | acetonitrile | 3 | 94 |
| 11 | 3-phenylpropionic acid | β-phenetylamine | N-(β-phenetyl)-3-phenylpropion amide | ethyl acetate | 4 | 95 |
| 12 | 3-phenylpropionic acid | β-phenetylamine | N-(β-phenetyl)-3-phenylpropion amide | tetrahydrofuran | 3 | 94 |
| 13 | 3-phenylpropionic acid | β-phenetylamine | N-(β-phenetyl)-3-phenylpropion amide | tetrahydrofurane/water = 9/1 | 4 | 92 |
| 14 | 3-phenylpropionic acid | β-phenetylamine | N-(β-phenetyl)-3-phenylpropion amide | isopropyl alcohol | 4 | 91 |
| 15 | hexanoic acid | β-phenetylamine | N-(β-phenetyl)-3-hexan amide | tetrahydrofuran | 4 | 93 |
| 16 | hexanoic acid | β-phenetylamine | N-(β-phenetyl)-3-hexan amide | methanol | 5 | 95 |
| 17 | 3-phenyl-2-propenoic acid | β-phenetylamine | N-(β-phenetyl)-3-phenyl-2-propen amide | tetrahydrofuran | 3 | 92 |
| 18 | 3-phenyl-2-propenoic acid | β-phenetylamine | N-(β-phenetyl)-3-phenyl-2-propen amide | methanol | 3 | 96 |
| 19 | propionic acid | β-phenetylamine | N-(β-phenetyl)propion amide | tetrahydrofuran | 3 | 94 |
| 20 | pivalic acid | β-phenetylamine | N-(β-phenetyl)pival amide | tetrahydrofuran | 3 | 92 |
| 21 | pivalic acid | β-phenetylamine | N-(β-phenetyl)pival amide | methanol | 3 | 95 |
| 22 | p-methoxybenzoic acid | β-phenetylamine | N-(β-phenetyl)-p-methoxybenz amide | tetrahydrofuran | 4 | 94 |
| 23 | p-methoxybenzoic acid | benzylamine | N-benzyl-p-methoxybenz amide | tetrahydrofuran | 3 | 93 |
| 24 | p-methoxybenzoic acid | benzylamine | N-benzyl-p-methoxybenz amide | methanol | 3 | 96 |
| 25 | p-methoxybenzoic acid | diethylamine | N-diethyl-p-methoxybenz amide | tetrahydrofuran | 4 | 92 |
| 26 | p-methoxybenzoic acid | diethylamine | N-diethyl-p-methoxybenz amide | methanol | 4 | 94 |

TABLE 2-continued

| Ex. | Carboxylic acid compound | Amine compound | Product | Solvent | Reaction time (hrs) | Yield (%) |
|---|---|---|---|---|---|---|
| 27 | p-methoxybenzoic acid | cyclohexylamine | N-cyclohexyl-p-methoxybenz amide | tetrahydrofuran | 3 | 94 |
| 28 | benzoic acid | β-phenetylamine | N-(β-Phenetyl)benz amide | tetrahydrofuran | 4 | 95 |
| 29 | benzoic acid | β-phenetylamine | N-(β-phenetyl)benz amide | methanol | 3 | 93 |
| 30 | p-nitrobenzoic acid | β-phenetylamine | N-(β-phenetyl)-p-nitrobenz amide | tetrahydrofuran | 3 | 91 |
| 31 | p-nitrobenzoic acid | β-phenetylamine | N-(β-phenetyl)-p-nitrobenz amide | methanol | 3 | 94 |
| 32 | p-hydroxybenzoic acid | β-phenetylamine | N-(β-phenetyl)-p-hydroxybenz amide | methanol | 4 | 92 |

Example 36

Into a 50-ml egg plant-type flask were added 3.01 g (0.01 mol) of a (Z)-2-(2-tert-butoxycarbonylaminothiazol-4-yl)-2-methoxyiminoacetic acid as a carboxylic acid compound, 3.28 g (0.01 mol) of a 7-amino-3-acetoxymethyl-3-cephem-4-carboxylic acid tert-butyl ester as an amine compound and 50 ml of a methylene chloride as a solvent, which were then stirred at room temperature for 10 minutes followed by the addition of 3.02 g (0.01 mol) of the same 4-(4,6-dimethoxy-1,3,5-triazin-2-yl)-4-methylmorpholinium chloride having a water content of 8.4% by weight as the one prepared in Example 1 as a condensing agent to effect the reaction at room temperature for 3 hours.

After the reaction, the after-treatment was conducted in the same manner as in Example 1 to obtain 5.84 g of a 7-[(Z)-2-(2-tert-butoxycarbonylaminothiazol-4-yl)-2-methoxyiminoacetic acid amide]-3-cephem-4-carboxylic acid tert-butyl ester (yield, 93%).

Examples 37 to 42

Amide compounds were obtained by conducting the same operation as that of Example 36 but using 2-aminothiazolyl acetic acid derivatives shown in Table 3 as carboxylic acid compounds and solvents shown in Table 3. The results were as shown in Table 3.

TABLE 3

| Ex. | 2-Aminothiazolacetic acid derivative | Product | Solvent | Reaction time (hrs) | Yield (%) |
|---|---|---|---|---|---|
| 37 | (Z)-2-(2-tert-butoxycarbonylaminothiazol-4-yl)-2-methoxyiminoacetic acid | tert-butyl 7-[(Z)-2-(2-tert-butoxycarbonylaminothiazol-4-yl)-2-methoxyiminoacetic acid]amide-3-cephem-4-carboxylate | tetrahydrofurane | 4 | 90 |
| 38 | (Z)-2-(2-aminothiazol-4-yl)-2-methoxyiminoacetic acid | tert-butyl 7-[(Z)-2-(2-aminothiazol-4-yl)-2-methoxyiminoacetic acid]amide-3-cephem-4-carboxylate | tetrahydrofurane | 3 | 94 |
| 39 | (Z)-2-(2-aminothiazol-4-yl)-2-methoxyiminoacetic acid | tert-butyl 7-[(Z)-2-(2-aminothiazol-4-yl)-2-methoxyiminoacetic acid]amide-3-cephem-4-carboxylate | methylene chloride | 3 | 90 |
| 40 | (Z)-2-(2-aminothiazol-4-yl)-2-(1-tert-butoxycarbonyl-1-ethoxy)iminoacetic acid | tert-butyl 7-[(Z)-2-(2-aminothiazol-4-yl)-2-(1-tert-butoxycarbonyl-1-methylethoxy)iminoacetic acid]amide-3-cephem-4-carboxylate | methylene chloride | 4 | 95 |
| 41 | (Z)-2-(2-aminothiazol-4-yl)-2-(1-tert-butoxycarbonyl-1-ethoxy)iminoacetic acid | tert-butyl 7-[(Z)-2-(2-aminothiazol-4-yl)-2-(1-tert-butoxycarbonyl-1-methylethoxy)iminoacetic acid]amide-3-cephem-4-carboxylate | tetrahydrofurane | 5 | 96 |
| 42 | (Z)-2-(2-chloroacetylaminothiazol-4-yl)-2-methoxyiminoacetic acid | tert-butyl 7-[(Z)-2-(2-chloroacetylaminothiazol-4-yl)-2-methoxyiminoacetic acid]amide 3-cephem-4-carboxylate | methylene chloride | 4 | 91 |

Examples 43 to 52

Amide compounds were obtained by conducting the same operation as that of Example 36 but using a (Z)-2-(2-aminothiazol-4-yl)-2-methoxyiminoacetic acid which is a 2-aminothiazoleacetic acid derivative as a carboxylic acid compound and 7-aminocephalosporanic acid derivatives shown in Table 4 as amine compounds. The results were as shown in Table 4.

Example 54

Into a 100-ml egg plant-type flask were added 5.30 g (0.02 mols) of an N-tert-butoxycarbonyl-L-phenylalanine as a carboxylic acid compound, 3.58 g (0.02 mols) of an L-phenylalaninemethyl ester as an amine compound and 50 ml of a methylene chloride as a solvent, which were then stirred at room temperature for 10 minutes. Then, 6.85 g (0.02 mols) of the same 4-(4,6-dimethoxy-1,3,5-triazin-2-

TABLE 4

| Example | 7-Aminocephalosporanic acid derivative | Product | Yield (%) |
|---|---|---|---|
| 43 | tert-butyl 7-amino-3-cephem-4-carboxylate | tert-butyl 7-[(Z)-2-(2-aminothiazol-4-yl)-2-methoxyiminoacetamide]-3-cephem-4-carboxylate | 92 |
| 44 | tert-butyl 7-amino-3-chloro-3-cephem-4-carboxylate | tert-butyl 7-[(Z)-2-(2-aminothiazol-4-yl)-2-methoxyiminoacetamide]-3-chloro-3-cephem-4-carboxylate | 92 |
| 45 | tert-butyl 7-amino-3-iodole-3-cephem-4-carboxylate | tert-butyl 7-[(Z)-2-(2-aminothiazol-4-yl)-2-methoxyiminoacetamide]-3-iodemethyl-3-cephem-4-carboxylate | 94 |
| 46 | tert-butyl 7-amino-3-(2-furalcarbonylthiomethyl)-3-cephem-4-carboxylate | tert-butyl 7-[(Z)-2-(2-aminothiazol-4-yl)-2-methoxyiminoacetamide]-3-(2-furalcarbonylthiomethyl)-3-cephem-4-carboxylate | 91 |
| 47 | tert-butyl 7-amino-3-[(1,2,3-thiadiazol-5-yl)thiomethyl]-3-cephem-4-carboxylate | tert-butyl 7-[(Z)-2-(2-aminothiazol-4-yl)-2-methoxyiminoacetamide]-3-[(1,2,3-thiadiazol-5-yl)thiomethyl]-3-cephem-4-carboxyl | 92 |
| 48 | tert-butyl 7-amino-3-[(1-methyltetrazol-5-yl)thiomethyl]-3-cephem-4-carboxylate | tert-butyl 7-[(Z)-2-(2-aminothiazol-4-yl)-2-methoxyiminoacetamide]-3-[(1-methyltetrazoly-5-yl)thiomethyl]-3-cephem-4-carboxylate | 92 |
| 49 | tert-butyl 7-amino-3-[(Z)-2-(1,2,3-thiadiazol-4-yl)ethenyl]-3-cephem-4-carboxylate | tert-butyl 7-[(Z)-2-(2-aminothiazol-4-yl)-2-methoxyiminoacetamide]-3-[(Z)-2-(1,2,3-thiadiazol-4-yl)ethenyl]-3-cephem-4-carboxylate | 90 |
| 50 | tert-butyl 7-amino-3-[(5-methyltetrazol-3-yl)methyl]-3-cephem-4-carboxylate | tert-butyl 7-[(Z)-2-(2-aminothiazol-4-yl)-2-methoxyiminoacetamide]-3-[(5-methyltetrazol-3-yl)methyl]-3-cephem-4-carboxylate | 91 |
| 51 | tert-butyl 7-amino-3-[(Z)-2-(4-methylthiazol-5-yl)ethenyl]-3-cephem-4-carboxylate | tert-butyl 7-[(Z)-2-(2-aminothiazol-4-yl)-2-methoxyiminoacetamide]-3-[(Z)-2-(4-methylthiadizol-5-yl)ethenyl]-3-cephem-4-carboxylate | 89 |
| 52 | tert-butyl 7-amino-3-[(1H-1,2,3-triazol-5-yl)thiomethylthio]-3-cephem-4-carboxylate | tert-butyl 7-[(Z)-2-(2-aminothiazol-4-yl)-2-methoxyiminoacetamide]-3-[(1H-1,2,3-triazol-5-yl)thiomethylthio]-3-cephem-4-carboxylate | 92 |

Example 53

Into a 100-ml egg plant-type flask were added 5.30 g (0.02 mols) of an N-tert-butoxycarbonyl-L-phenylalanine as a carboxylic acid compound, 2.42 g (0.02 mols) of a β-phenetylamine as an amine compound and 50 ml of a methylene chloride as a solvent, which were then stirred at room temperature for 10 minutes followed by the addition of 6.85 g (0.02 mols) of the same 4-(4,6-dimethoxy-1,3,5-triazin-2-yl)-4-methylmorpholinium chloride having a water content of 19.1% by weight as the one prepared in Example 5 as a condensing agent to effect the reaction at room temperature for 3 hours.

After the reaction, 100 ml of water was added thereto to separate the solution. Thereafter, the extraction operation was conducted twice with 30 ml of a methylene chloride. The separated methylene chloride solution was collected, and the organic layer was washed with 30 ml of a saturated sodium carbonate aqueous solution, 30 ml of a 1N hydrochloric acid and 30 ml of water. The obtained organic layer was dried on magnesium sulfate, condensed, and the residue was isolated and refined by using a silica gel column chromatography to obtain 7.14 g of an N-tert-butoxycarbonyl-L-phenylalanine-β-phenetylamide (yield, 97%).

yl)-4-methylmorpholinium chloride having a water content of 19.1% by weight as the one prepared in Example 5 was slowly added thereto as a condensing agent to effect the reaction at room temperature for 3 hours.

After the reaction, 100 ml of water was added thereto to separate the solution. Thereafter, the extraction operation was conducted twice with 30 ml of a methylene chloride. The separated methylene chloride solution was collected, and the organic layer was washed with 30 ml of a saturated sodium carbonate aqueous solution, 30 ml of a 1N hydrochloric acid and 30 ml of water. The obtained organic layer was dried on magnesium sulfate, condensed and was isolated and refined by using a silica gel column chromatography to obtain 8.18 g of an N-tert-butoxycarbonyl-L-phenylalanyl-L-phenylalaninemethyl ester (yield, 96%).

Examples 55 to 67

Amide compounds were obtained by conducting the operation same as that of Example 54 but using amino acids of which the amino group is protected shown in Table 5 as carboxylic acid compounds and using amino acids of which the carboxyl group is protected shown in Table 5 as amine compounds. The results were as shown in Table 5.

TABLE 5

| Ex. | Carboxylic acid compound | Amine compound | Product | Yield (%) |
|---|---|---|---|---|
| 55 | N-benzyloxycarbonyl-L-phenylalanine | L-phenylalaninemethyl ester | N-benzyloxycarbonyl-L-phenylalanyl-L-phenylalaninemethyl ester | 97 |
| 56 | N-acetyl-L-phenylalanine | L-phenylalaninemethyl ester | N-acetyl-L-phenylalanyl-L-phenylalaninemethyl ester | 95 |
| 57 | N-tert-butoxycarbonyl-D-phenylalanine | L-phenylalaninemethyl ester | N-tert-butoxycarbonyl-D-phenylalanyl-L-phenylalaninemethyl ester | 95 |
| 58 | N-tert-butoxycarbonyl-L-phenylalanine | L-phenylalaninebenzyl ester | N-tert-butoxycarbonyl-L-phenylalanyl-L-phenylalaninebenzyl ester | 94 |
| 59 | N-methoxycarbonyl-L-phenylalanine | L-phenylalanineethyl ester | N-methoxycarbonyl-L-phenylalanyl-L-phenylalanineethyl ester | 93 |
| 60 | N-tert-butoxycarbonyl-L-phenylalanine | L-phenylalalanylamide | N-tert-butoxycarbonyl-L-phenylalanyl-L-phenylalanylamide | 94 |
| 61 | N-tert-butoxycarbonylglycine | glycinemethyl ester | N-tert-butoxycarbonylglycylglycinemethyl ester | 97 |
| 62 | N-tert-butoxycarbonyl-L-phenylalanine | L-leucinemethyl ester | N-tert-butoxycarbonyl-L-phenylalanyl-L-leucinemethyl ester | 95 |
| 63 | N-tert-butoxycarbonyl-L-phenylalanine | L-alaninemethyl ester | N-tert-butoxycarbonyl-L-phenylalanyl-L-alaninemethyl ester | 92 |
| 64 | N-tert-butoxycarbonyl-L-alanine | L-alanine-tert-butyl ester | N-tert-butoxycarbonyl-L-alanyl-L-alanine-tert-butyl ester | 96 |
| 65 | N-tert-butoxycarbonyl-L-methionine | α-Methylalaninemethyl | N-tert-butoxycarbonyl-L-methionyl-α-methylalaninemethyl ester | 92 |
| 66 | N-tert-butoxycarbonyl-α-Methylalanine | L-alaninemethyl ester | N-tert-butoxycarbonyl-α-Methylalanyl-L-alaninemethyl ester | 91 |
| 67 | N-tert-butoxycarbonyl-L-leucine | L-phenylalaninemethyl ester | N-tert-butoxycarbonyl-L-leucyl-L-phenylalaninemethyl ester | 95 |

Example 68

Into a 100-ml egg plant-type flask were added 3.00 g (0.02 mols) of a 3-phenylpropionic acid as a carboxylic acid compound, 2.22 g (0.022 mols) of a 4-methylmorpholine as a tertiary amine compound and 50 ml of methanol as an alcohol compound, which were then stirred at room temperature for 10 minutes. Then, 6.35 g (0.02 mols) of the same 4-(4,6-dimethoxy-1,3,5-triazin-2-yl)-4-methylmorpholinium chloride having a water content of 12.8% by weight as the one prepared in Example 4 was added thereto as a condensing agent to effect the reaction at room temperature for 4 hours.

After the reaction, methanol was distilled off, 100 ml of water was added thereto, and the extraction operation was conducted twice with 30 ml of a methylene chloride. The separated methylene chloride solution was collected, and the organic layer was washed with 20 ml of a saturated sodium carbonate aqueous solution, 20 ml of a 1N hydrochloric acid and 20 ml of water. The obtained organic phase was dried on magnesium sulfate, the methylene chloride was distilled off, and the residue was isolated and refined by using a silica gel column chromatography to obtain 3.05 g of a methyl 3-phenylpropionate (yield, 93%).

Examples 69 to 83

Ester compounds were obtained by conducting the operation same as that of Example 68 but using carboxylic acid compounds and alcohol compounds shown in Table 6 and using the condensing agent and the N-methylmorpholine in amounts as shown in FIG. 6. The results were as shown in Table 6.

TABLE 6

| Ex. | Carboxylic acid compound | Alcohol compound | Product | Condensing agent (mols) | 4-Methylmorpholine (mols) | Reaction time (hrs) | Yield (%) |
|---|---|---|---|---|---|---|---|
| 69 | 3-phenylpropionic acid | methanol | methyl 3-phenylpropionate | 0.024 | 0.002 | 5 | 91 |
| 70 | 3-phenylpropionic acid | methanol | methyl 3-phenylpropionate | 0.04 | 0.024 | 2 | 97 |
| 71 | 3-phenylpropionic acid | ethanol | methyl 3-phenylpropionate | 0.024 | 0.002 | 4 | 73 |
| 72 | 3-phenylpropionic acid | ethanol | methyl 3-phenylpropionate | 0.04 | 0.024 | 2 | 97 |
| 73 | 3-phenylpropionic acid | 1-propanol | n-propyl 3-phenylpropionate | 0.04 | 0.024 | 2 | 98 |
| 74 | 3-phenylpropionic acid | 2-propanol | isopropyl 3-phenylpropionate | 0.04 | 0.024 | 6 | 93 |
| 75 | hexanoic acid | methanol | methyl hexanoate | 0.022 | 0.022 | 4 | 94 |
| 76 | hexanoic acid | ethanol | methyl hexanoate | 0.022 | 0.022 | 4 | 93 |
| 77 | 3-phenyl-2-propenoic acid | methanol | methyl 3-phenyl-2-propenoate | 0.04 | 0.024 | 2 | 98 |
| 78 | 3-phenyl-2-propenoic acid | ethanol | ethyl 3-phenyl-2-propenoate | 0.04 | 0.024 | 2 | 98 |
| 79 | p-nitrobenzoic acid | methanol | methyl p-nitrobenzoate | 0.024 | 0.024 | 3 | 95 |
| 80 | terephthalic acid | methanol | dimethyl terephthalate | 0.048 | 0.044 | 4 | 94 |
| 81 | isophthalic acid | methanol | dimethyl isophthalate | 0.048 | 0.044 | 3 | 92 |
| 82 | p-methoxybenzoic acid | methanol | methyl p-methoxybenzoate | 0.024 | 0.024 | 3 | 96 |
| 83 | p-methoxybenzoic acid | ethanol | ethyl p-methoxybenzoate | 0.024 | 0.024 | 3 | 93 |

Example 84

Into a 100-ml egg plant-type flask were added 5.30 g (0.02 mols) of an N-tert-butoxycarbonyl-L-phenylalanine as a carboxylic acid compound, 2.42 g (0.024 mols) of a 4-methylmorpholine as a tertiary amine compound and 100 ml of methanol as an alcohol compound, which were then stirred at room temperature for 10 minutes. Then, 6.85 g (0.02 mols) of the same 4-(4,6-dimethoxy-1,3,5-triazin-2-yl)-4-methylmorpholinium chloride having a water content of 19.1% by weight as the one prepared in Example 5 was added thereto as a condensing agent to effect the reaction at room temperature for 3 hours.

After the reaction, methanol was distilled off, 100 ml of water was added thereto, and the extraction operation was conducted twice with 30 ml of a methylene chloride. The separated methylene chloride solution was collected, and the organic layer was washed with 20 ml of a saturated sodium carbonate aqueous solution, 20 ml of a 1N hydrochloric acid and 20 ml of water. The obtained organic layer was dried on magnesium sulfate, condensed and the residue was isolated and refined by using a silica gel column chromatography to obtain 5.36 g of an N-tert-butoxycarbonyl-L-phenylalaninemethyl ester (yield, 96%).

Examples 85 to 97

Ester compounds were obtained by conducting the operation same as that of Example 84 but using the protected amino acids shown in Table 7 as carboxylic acid compounds. The results were as shown in Table 7.

Example 98

Into a 100-ml egg plant-type flask were added 3.00 g (0.02 mols) of a 3-phenylpropionic acid as a carboxylic acid compound, 6.06 g (0.06 mols) of a 4-methylmorpholine as a tertiary amine compound, 2.38 g (0.022 mols) of a benzyl alcohol as an alcohol compound and 50 ml of a tetrahydrofurane as a solvent, which were then stirred at room temperature for 10 minutes. Then, 6.85 g (0.02 mols) of the same 4-(4,6-dimethoxy-1,3,5-triazin-2-yl)-4-methylmorpholinium chloride having a water content of 19.1% by weight as the one prepared in Example 5 was added thereto as a condensing agent to effect the reaction at room temperature for 24 hours.

After the reaction, tetrahydrofurane was distilled off, 100 ml of water was added thereto, and the extraction operation was conducted twice with 30 ml of a methylene chloride. The separated methylene chloride solution was collected, and the organic layer was washed with 20 ml of a saturated sodium carbonate aqueous solution, 20 ml of a 1N hydrochloric acid and 20 ml of water. The obtained organic phase was dried on magnesium sulfate, the methylene chloride was distilled off, and the residue was isolated and refined by using a silica gel column chromatography to obtain 4.51 g of a benzyl 3-phenylpropionate (yield, 94%).

Example 99

Into a 100-ml egg plant-type flask were added 3.00 g (0.02 mols) of a 3-phenylpropionic acid as a carboxylic acid compound, 2.42 g (0.02 mols) of a β-phenetylamine as an amine compound and 50 ml of an ethyl acetate (containing 300 ppm of water) as a solvent, which were then stirred at room temperature for 10 minutes, followed by the addition of 6.35 g (0.02 mols) of the same 4-(4,6-dimethoxy-1,3,5-triazin-2-yl)-4-methylmorpholinium chloride having a water content of 12.8% by weight as the one prepared in Example 4 as a condensing agent to effect the reaction at room temperature for 3 hours.

After the reaction, 100 ml of water was added thereto to separate the solution, and the extraction operation was conducted twice with 30 ml of the ethyl acetate. The separated ethyl acetate solution was collected, and the organic phase was washed with 30 ml of a saturated sodium carbonate aqueous solution, 30 ml of a 1N hydrochloric acid and 30 ml of water. The obtained organic phase was dried on magnesium sulfate, the ethyl acetate was distilled off, and the residue was isolated and refined by using a silica gel column chromatography to obtain 4.81 g of an N-(β-phenetyl)-3-phenylpropion amide (yield, 95%).

Next, the operation same as the one described above was conducted by using, as a solvent, 50 ml of the ethyl acetate (water content of 28,000 ppm) recovered by the above operation to obtain 4.76 g of the N-(β-phenetyl)-3-phenylpropion amide (yield, 94%).

The same operation was further effected by using, as a solvent, 50 ml of the ethyl acetate (water content of 28,100 ppm) that was recovered to obtain 4.76 g of the N-(β-phenetyl)-3-phenylpropion amide (yield, 94%). Thus, there was quite no change in the yield.

Example 100

Into a 100-ml egg plant-type flask were added 2.65 g (0.01 mol) of an N-tert-butoxycarbonylphenylalanine, 1.79 g (0.01 mmol) of a Phenylalaninemethyl ester and 25 ml of a dichloromethane, which were then stirred at room temperature for 10 minutes.

Next, into a 200-ml egg plant-type flask were added 27.3 g of the same 4-(4,6-dimethoxy-1,3,5-triazin-2-yl)-4-methylmorpholinium chloride (water content of 8.4% by weight and purity of 99.5%) as the one obtained in Example

TABLE 7

| Ex. | Carboxylic acid compound | Product | Yield (%) |
| --- | --- | --- | --- |
| 85 | N-benzyloxycarbonyl-L-phenylalanine | N-benzyloxycarbonyl-L-phenylalaninemethyl ester | 96 |
| 86 | N-acetyl-L-phenylalanine | N-acetyl-L-phenylalaninemethyl ester | 95 |
| 87 | N-tert-butoxycarbonyl-D-phenylalanine | N-tert-butoxycarbonyl-D-phenylalaninemethyl ester | 97 |
| 88 | N-tert-butoxycarbonyl-L-alanine | N-tert-butoxycarbonyl-L-alaninemethyl ester | 95 |
| 89 | N-methoxycarbonyl-L-phenylalanine | N-methoxycarbonyl-L-phenylalaninemethyl ester | 94 |
| 90 | N-tert-butoxycarbonyl-L-leucine | N-tert-butoxycarbonyl-L-leucinemethyl ester | 93 |
| 91 | N-tert-butoxycarbonylglycine | N-tert-butoxycarbonylglycinemethyl ester | 95 |
| 92 | N-tert-butoxycarbonylglutamic acid | methyl N-tert-butoxycarbonyl glutamate | 94 |
| 93 | N-tert-butoxycarbonyl-L-proline | N-tert-butoxycarbonyl-L-prolinemethyl ester | 95 |
| 94 | N-tert-butoxycarbonyl-β-Alanine | N-tert-butoxycarbonyl-β-alaninemethyl ester | 94 |
| 95 | N-tert-butoxycarbonyl-L-Methionine | N-tert-butoxycarbonyl-L-methioninemethyl ester | 92 |
| 96 | N-tert-butoxycarbonyl-α-Methylalanine | N-tert-butoxycarbonyl-α-methylalaninemethyl ester | 94 |
| 97 | N-tert-butoxycarbonyl-L-phenylglycine | N-tert-butoxycarbonyl-L-phenylglycinemethyl ester | 97 |

1 and 72.7 g of water, which were stirred and dissolved at 20° C. to separately prepare the condensing agent of the invention. 11.08 Grams (0.01 mol) of the thus prepared condensing agent of the invention was slowly added to the above 100-ml egg plant-type flask to effect the reaction at room temperature for 3 hours.

After the reaction, 25 ml of a dichloromethane was added thereto, and the mixture was washed with 50 ml of water to separate the organic layer which was then dried on magnesium sulfate, condensed and was isolated and refined by using a silica gel column chromatography to obtain 4.05 g of an N-tert-butoxycarbonyl-L-phenylalanyl-L-phenylalaninemethyl ester (yield, 95.0%).

It was thus confirmed that the condensing agent in the form of an aqueous solution of the present invention exhibited the function as a condensing agent.

Example 101

The remainder of the condensing agent of the invention in the form of an aqueous solution prepared in Example 100 was freeze-preserved at −20° C. After one month has passed, the condensing agent was thawed to measure the purity of the 4-(4,6-dimethoxy-1,3,5-triazin-2-yl)-4-methylmorpholinium chloride by using a high-performance liquid chromatography to be 99.3%, from which it was confirmed that the condensing agent and the quaternary ammonium salt of the present invention had been stably preserved.

Example 102

The reaction was carried out in the same manner as in Example 100 but using the condensing agent of the present invention thawed in Example 101 to obtain 4.04 g of an N-tert-butoxycarbonyl-L-phenylalanyl-L-phenylalaninemethyl ester (yield, 94.8%), from which it was confirmed that the condensing agent of the present invention after freeze-preserved maintained properties of before being preserved.

Examples 103 to 105

The condensing agents of the present invention was prepared in the same manner as in Example 1 by using the same 4-(4,6-dimethoxy-1,3,5-triazin-2-yl)-4-methylmorpholinium chloride (water content of 8.4% by weight, purity of 99.5%) as the one obtained in Example 1, but changing its amount and the amount of water to be mixed as shown in Table 8. The condensing agents of the invention were freeze-preserved in the same manner as in Example 101 and were, then, thawed, to measure the purity of the 4-(4,6-dimethoxy-1,3,5-triazin-2-yl)-4-methylmorpholinium chloride in the same manner as in Example 102. The results were as shown in Table 8.

TABLE 8

| Example | Amount of 4-(4,6-dimethoxy-1,3,5-triazin-2-yl)-4-methylmorpholinium chloride (g) | Amount of water (g) | Purity after one month (%) |
| --- | --- | --- | --- |
| 103 | 21.8 | 78.2 | 99.3 |
| 104 | 10.9 | 89.1 | 99.2 |
| 105 | 5.5 | 94.5 | 99.2 |

Comparative Example 3

The condensing agent of the present invention prepared in the same manner as in Example 100 was preserved without being frozen but at 20 to 25° C. for one month. After preserved, the quaternary ammonium salt was measured for its purity by using a high-performance liquid chromatography to be 4.8%

Example 106

Into a 500-ml four neck distillation flask were added 21.95 g (0.125 mols) of a 2-chloro-4,6-dimethoxy-1,3,5-triazine, 250 ml of an ethyl acetate and 6.75 g (0.375 mols) of water, which were, then, stirred at 5 to 10° C. for 10 minutes. Then, 13.25 g (0.131 mols) of a 4-methylmorpholine was added thereto to effect the reaction at 5 to 10° C. for 6 hours. The precipitated crystals were filtrated by means of suction, washed with 100 ml of the ethyl acetate, and were dried at room temperature under a reduced pressure for 16 hours to obtain 32.62 g of a white solid of a 4-(4,6-dimethoxy-1,3,5-triazin-2-yl)-4-methylmorpholinium chloride represented by the above-mentioned general formula (I) as a quaternary ammonium salt. The white solid contained water in an mount of 0.6% by weight and its yield was 93.8%.

Analysis of the white solid by using a high-performance liquid chromatography indicated the purity (ratio of a peak area of the quaternary ammonium salt occupying the peak areas of the components other than water) to be 99.8% in terms of area %, but a peak of the 2-chloro-4,6-dimethoxy-1,3,5-triazine could not be detected (limit of detection is 0.001% by weight in terms of the content of the triazine compound). Next, the white solid was preserved at 20 to 25° C. for 3 weeks and was measured for its purity to be 97.5%.

Example 107

Into a 500-ml four neck distillation flask were added 17.56 g (0.1 mol) of a 2-chloro-4,6-dimethoxy-1,3,5-triazine, 200 ml of a tetrahydrofuran and 9.6 g (0.3 mols) of methanol, which were, then, stirred at 5 to 10° C. for 10 minutes. Then, 10.6 g (0.105 mols) of a 4-methylmorpholine was added thereto to effect the reaction at 5 to 10° C. for 4 hours. The precipitated crystals were filtrated by means of suction, washed with 100 ml of a tetrahydrofuran, and were dried at room temperature under a reduced pressure for 3 hours to obtain 27.02 g of a white solid of a 4-(4,6-dimethoxy-1,3,5-triazin-2-yl)-4-methylmorpholinium chloride represented by the above-mentioned general formula (I) as a quaternary ammonium salt. The white solid contained water in an mount of 0.3% by weight and its yield was 97.4%.

Analysis of the white solid by using a high-performance liquid chromatography indicated the purity (ratio of a peak area of the quaternary ammonium salt occupying peak areas of the components other than water) to be 99.7% in terms of area %. The content of the 2-chloro-4,6-dimethoxy-1,3,5-triazine was 0.1% by weight. Next, parts of the white solid were preserved at 20 to 25° C., at 5° C. and at −20° C., respectively, for 3 weeks and were measured for their purities to be 97.5%, 99.6% and 99.7%, respectively. The white powder was further preserved at 5° C. for two months and was measured for its purity to be 99.3%.

Example 108

Into a 500-ml four neck distillation flask were added 17.56 g (0.1 mol of a 2-chloro-4,6-dimethoxy-1,3,5-triazine, 200 ml of a tetrahydrofuran and 9.6 g (0.3 mols) of methanol, which were, then, stirred at 5 to 10° C. for 10 minutes. Then, 10.6 g (0.105 mols) of a 4-methylmorpholine was added thereto to effect the reaction at 5 to 10° C. for 3 hours. The precipitated crystals were filtrated by means of suction, washed with 100 ml of a tetrahydrofuran, and were dried at room temperature under a reduced pressure for 3 hours to obtain 26.88 g of a white solid of a 4-(4,6-dimethoxy-1,3,5-triazin-2-yl)-4-methylmorpholinium chloride represented by the above-mentioned general formula (I) as a quaternary ammonium salt. The white solid contained water in an mount of 0.3% by weight and its yield was 96.9%.

Analysis of the white solid by using a high-performance liquid chromatography indicated the purity (ratio of a peak area of the quaternary ammonium salt occupying peak areas of the components other than water) to be 99.5% in terms of area %. The content of the 2-chloro-4,6-dimethoxy-1,3,5-triazine was 0.3% by weight. Next, parts of the white solid were preserved at 20 to 25° C., at 5° C. and at −20° C., respectively, for 3 weeks and were measured for their purities to be 96.8%, 99.1% and 99.4%, respectively. The white powder was further preserved at 5° C. for two months and was measured for its purity to be 98.8%.

Comparative Example 4

Into a 500-ml four neck distillation flask were added 17.56 g (0.1 mol) of a 2-chloro-4,6-dimethoxy-1,3,5-triazine and 200 ml of a tetrahydrofuran, which were, then, stirred at 5 to 10° C. for 10 minutes. Then, 10.6 g (0.105 mols) of a 4-methylmorpholine was added thereto to effect the reaction at 5 to 10° C. for 6 hours. The precipitated crystals were filtrated by means of suction, washed with 100 ml of a tetrahydrofuran, and were dried at room temperature under a reduced pressure for 3 hours to obtain 26.1 g of a white solid of a 4-(4,6-dimethoxy-1,3,5-triazin-2-yl)-4-methylmorpholinium chloride represented by the above-mentioned general formula (I) as a quaternary ammonium salt. The white solid contained water in an mount of 0.4% by weight and its yield was 94.0%.

Analysis of the white solid by using a high-performance liquid chromatography indicated the purity (ratio of a peak area of the quaternary ammonium salt occupying peak areas of the components other than water) to be 95.8% in terms of area %. The content of the 2-chloro-4,6-dimethoxy-1,3,5-triazine was 3.4% by weight. Next, parts of the white solid were preserved at 20 to 25° C. and at 5° C., respectively, for 3 weeks and were measured for their purities to be 87.5% and 91.7%, respectively.

Industrial Applicability

According to the method of preserving the quaternary ammonium salt of the present invention, it is made possible to stably preserve the quaternary ammonium salt represented by the above-mentioned general formula (I) for extended periods of time without permitting it to be decomposed.

Besides, the quaternary ammonium salt preserved according to the preservation method of the present invention can be readily used as a condensing agent without the need of effecting the processing such as drying or activation, and is favorably used as a condensing agent in the preparation of carboxylic acid compound derivatives by condensing, for example, a carboxylic acid compound with an amine compound or an alcohol compound.

According to the preparation method of the present invention, further, the quaternary ammonium salt represented by the above-mentioned general formula (I) can be obtained in a short period of time in a highly stable state.

What is claimed is:

1. A method of preserving a quaternary ammonium salt having a purity equal to or less than 99.8%, the quaternary ammonium salt being represented by the following general formula (I),

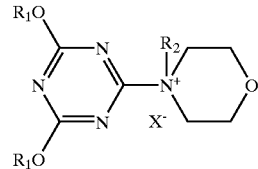

wherein $R_1$ is an alkyl group having 1 to 4 carbon atoms or an aryl group having 6 to 8 carbon atoms, $R_2$ is an alkyl group having 1 to 4 carbon atoms, and X is a halogen atom, said purity of quaternary ammonium salt being determined by chromatographic analysis peak area % measured by using a high-performance liquid chromatography and wherein water is not an impurity, the method comprising the steps of:

preparing a hydrous quaternary ammonium salt consisting of 60 to 99% by weight of said quaternary ammonium salt and 40 to 1% by weight of water by adjusting a content of water in the salt, and preserving the thus obtained hydrous quaternary ammonium salt.

2. A hydrous quaternary ammonium salt consisting of 60 to 99% by weight of a quaternary ammonium salt and 40 to 1% by weight of water having a purity equal to or less than 99.8%, the quaternary ammonium salt being represented by the following general formula (I),

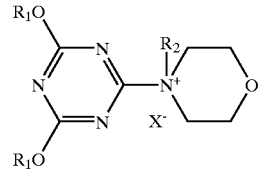

wherein $R_1$ is an alkyl group having 1 to 4 carbon atoms or an aryl group having 6 to 8 carbon atoms, $R_2$ is an alkyl group having 1 to 4 carbon atoms, and X is a halogen atom, said purity of quaternary ammonium salt being determined by chromatographic analysis peak area % measured by using a high-performance liquid chromatography and wherein water is not an impurity.

3. A method of preparing a hydrous quaternary ammonium salt according to claim 2, wherein said quaternary ammonium salt contains a triazine compound represented by the following formula (II) in an amount of less than 1% by weight, as an impurity,

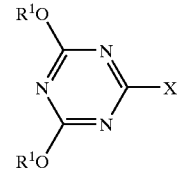

wherein $R_1$ is an alkyl group having 1 to 4 carbon atoms or an aryl group having 6 to 8 carbon atoms, and X is a halogen atom, and said triazine compound of the general formula (II) above is reacted with a morpholino compound represented by the following general formula (III),

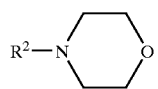

wherein $R_2$ is an alkyl group having 1 to 4 carbon atoms, with the proviso that the reaction being carried out in an organic solvent in the presence of water of an amount of from 0.1 to 10 mols per mol of the triazine compound and then adjusting the content of water coexisting with the quaternary ammonium salt to 1 to 40% by total weight of said quaternary ammonium salt and water.

* * * * *